(12) United States Patent
Miao et al.

(10) Patent No.: US 11,400,185 B2
(45) Date of Patent: Aug. 2, 2022

(54) BIOCOMPATIBLE SMART BIOMATERIALS WITH TUNABLE SHAPE CHANGING AND ENHANCED CYTOCOMPATIBILITY PROPERTIES

(71) Applicant: The George Washington University a Congressionally Chartered Not-for-Profit Corporation, Washington, DC (US)

(72) Inventors: Shida Miao, Arlington, VA (US); Wei Zhu, Washington, DC (US); Nathan J. Castro, Washington, DC (US); Lijie G. Zhang, Arlington, VA (US)

(73) Assignee: The George Washington University a Congressionally Chartered Not-for-Profit Corporation, Washington, DC (US)

( * ) Notice: Subject to any disclaimer, the term of this patent is extended or adjusted under 35 U.S.C. 154(b) by 687 days.

(21) Appl. No.: 15/754,938

(22) PCT Filed: Aug. 25, 2016

(86) PCT No.: PCT/US2016/048647
§ 371 (c)(1),
(2) Date: Feb. 23, 2018

(87) PCT Pub. No.: WO2017/035332
PCT Pub. Date: Mar. 2, 2017

(65) Prior Publication Data
US 2020/0237963 A1 Jul. 30, 2020

Related U.S. Application Data

(60) Provisional application No. 62/210,257, filed on Aug. 26, 2015.

(51) Int. Cl.
*A61L 27/50* (2006.01)
*A61L 27/18* (2006.01)
(Continued)

(52) U.S. Cl.
CPC ............ *A61L 27/50* (2013.01); *A61L 27/18* (2013.01); *A61L 27/3637* (2013.01); *A61L 27/56* (2013.01); *A61L 2400/16* (2013.01)

(58) Field of Classification Search
None
See application file for complete search history.

(56) References Cited

U.S. PATENT DOCUMENTS 3,066,997 A * 12/1962 Neher .................. C08G 18/36
8/94.21
8,394,492 B1 * 3/2013 Leventis ............. C04B 41/4853
428/319.3
(Continued)

FOREIGN PATENT DOCUMENTS

WO 2014-204634 A1 12/2014
WO 2014-205306 A1 12/2014

OTHER PUBLICATIONS

Lippincott et al., "Testing Shape Memory of Porous Polymer Tissue Engineering Scaffolds in Compression," ASME 2011 International Mechanical Engineering Congress and Exposition, Denver, Colorado, US, vol. 2, pp. 1-5 (Nov. 11-17, 2011). [Cited in International Search Report and Written Opinion in International Patent Application No. PCT/US2016/048647, dated Nov. 21, 2016.].
(Continued)

*Primary Examiner* — Peter A Salamon
(74) *Attorney, Agent, or Firm* — Polsinelli LLP; Kory D. Christensen

(57) ABSTRACT

The present application relates to biocompatible polymers that exhibit a shape-memory effect, devices made using the
(Continued)

materials and methods of producing such materials and devices.

8 Claims, 14 Drawing Sheets

(51) Int. Cl.
*A61L 27/36* (2006.01)
*A61L 27/56* (2006.01)

(56) References Cited

U.S. PATENT DOCUMENTS

2006/0051394 A1* 3/2006 Moore .................... A61L 27/18
424/423
2010/0084784 A1* 4/2010 Jabbari .................. B29C 33/52
264/219

OTHER PUBLICATIONS

International Search Report and Written Opinion in International Patent Application No. PCT/US2016/048647, dated Nov. 21, 2016.

* cited by examiner

BIOCOMPATIBLE SMART BIOMATERIALS WITH TUNABLE SHAPE CHANGING AND ENHANCED CYTOCOMPATIBILITY PROPERTIES

CROSS-REFERENCE OF RELATED APPLICATION

This application is a National Stage Application under 35 U.S.C. § 371 of PCT/US2016/048647, filed Aug. 25, 2016, which in turn claims priority to U.S. Provisional Application No. 62/210,257 filed Aug. 26, 2015; the entire contents of both of which are hereby incorporated by reference.

This invention was made with Government support under Grant No. 1 DP2 OD019144-01 awarded by the Department of Health and Human Services, The National Institutes of Health (NIH). Support was also provided by the NIH Director's New Innovator Award (DP2EB020549). The Government has certain rights in the invention.

BACKGROUND

1. Technical Field

The currently claimed embodiments of this invention relates to biocompatible polymers that exhibit a shape-memory effect, devices made using the materials and methods of producing the materials and devices.

2. Discussion of Related Art

Polycaprolactone (PCL) is widely utilized in the development of shape memory biomaterials. However, the shape recovery temperature of PCL is always above human body temperature due to its high melting around 60° C., and the white opaque feature of PCL limits applications requiring easy observations.

Therefore, there remains a need for improved naturally derived smart biomaterials with tunable shape changing and enhanced cytocompatibility properties.

SUMMARY

An embodiment of the invention relates to a biomimetic scaffold for cell growth or tissue regeneration having a scaffold body including a shape memory polymer. The scaffold body has an initial open configuration in a first environmental condition and a compact configuration in a second environmental condition. The scaffold body, when in the compact configuration, reverts to the initial open configuration in response to being exposed to the first environmental condition. The scaffold body defines a network of a plurality of pores, the plurality of pores being of a sufficient size to allow for cellular nutrient perfusion and cellular waste removal, and the scaffold body is biocompatible.

An embodiment of the invention relates to a method for producing a biomimetic scaffold body for cell growth or tissue regeneration comprising providing a template structure comprising a sacrificial scaffold, the template structure suitable for containing a shape memory polymer composition; depositing a shape memory polymer composition into the template structure; cross-linking the shape memory polymer composition; and removing the sacrificial scaffold. The scaffold body has an initial open configuration in a first environmental condition and a compact configuration in a second environmental condition. The scaffold body, when in the compact configuration, reverts to the initial open configuration in response to the first environmental condition. The scaffold body defines a network of a plurality of pores corresponding to the removed sacrificial scaffold, the plurality of pores being of a sufficient size to allow for cellular nutrient perfusion and cellular waste removal, and the scaffold body is biocompatible.

An embodiment of the invention relates to a shape memory polymer composition having a cross-linker molecule comprising at least two isocyanate groups; a natural oil comprising a hydroxyl group cross-linked to at least one of the at least two isocyanate groups, thereby forming a natural oil-based polymeric network; and a biocompatible polymer comprising a hydroxyl group cross-linked to at least one of the at least two isocyanate groups, thereby forming a biocompatible polymer-based polymeric network. The natural oil and the biocompatible polymer are cross-linked to different isocyanate groups.

An embodiment of the invention relates to a method of forming a shape memory polymer including: preparing a shape memory polymer composition comprising a cross-linker molecule having at least two isocyanate groups; a natural oil having comprising a hydroxyl group; and a biocompatible polymer comprising a hydroxyl group. Cross-linking the shape memory polymer composition results in a hydroxyl group of the natural oil is cross-linked to at least one of the isocyanate groups and a hydroxyl group of the biocompatible polymer is cross-linked to at least one of the isocyanate groups. The natural oil and the biocompatible polymer are cross-linked to different isocyanate groups. The crosslinking of the natural oil to the cross-linker forms a natural oil-based polymeric network, and the cross-linking of the biocompatible polymer to the cross-linker forms a biocompatible polymer-based network.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Figure 1:
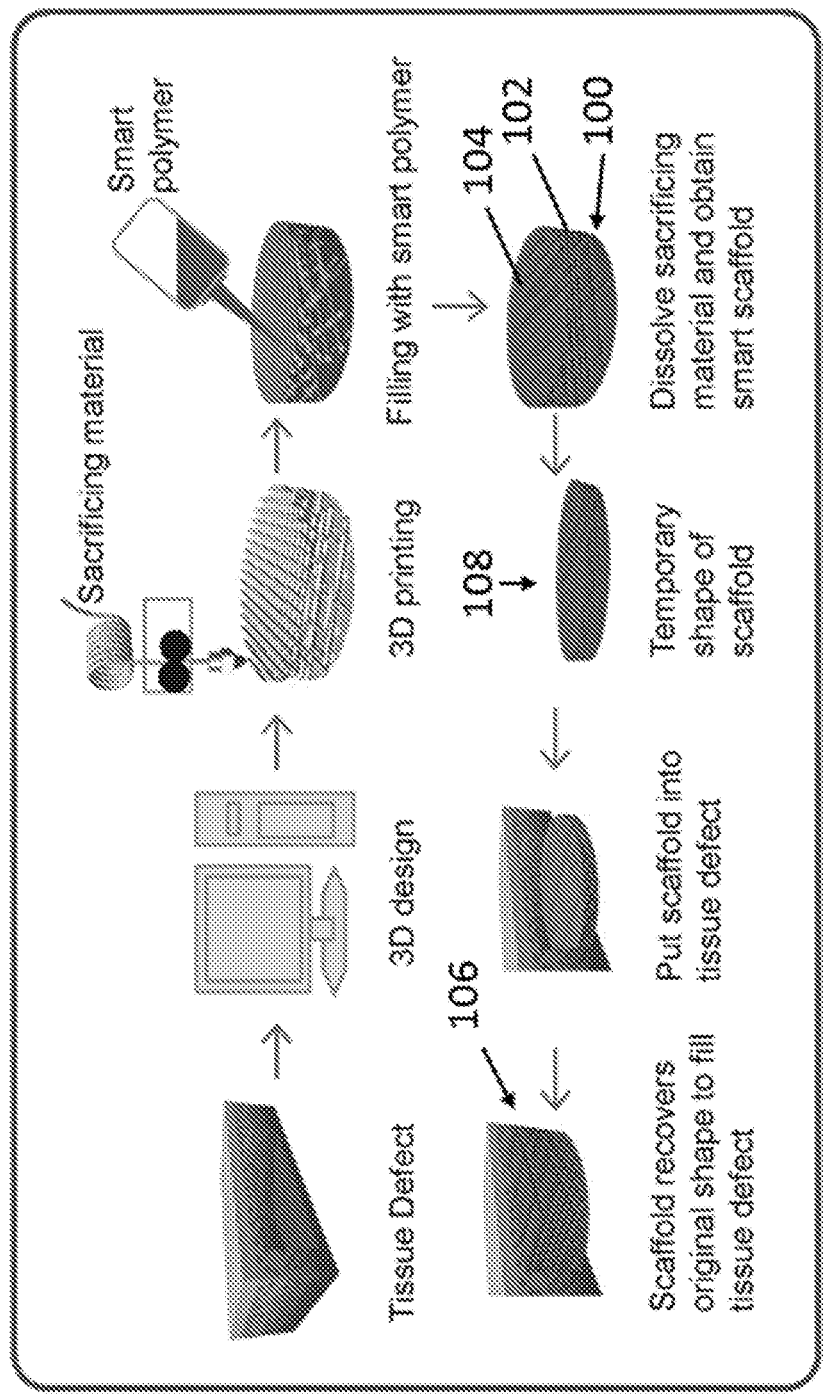
FIG. 1 is a schematic showing a process for preparing a biomedical scaffold according to a specific traumatic defect.

FIG. 1 shows an embodiment of the invention. The embodiment depicted in FIG. 1 relates to a biomimetic scaffold 100 for cell growth or tissue regeneration having a scaffold body 102 including a shape memory polymer 104. The scaffold body has an initial open configuration 106 in a first environmental condition and a compact configuration 108 in a second environmental condition. The scaffold body, when in the compact configuration, reverts to the initial open configuration in response to being exposed to the first environmental condition. The scaffold body defines a network of a plurality of pores, the plurality of pores being of a sufficient size to allow for cellular nutrient perfusion and cellular waste removal, and the scaffold body is biocompatible.

An embodiment of the invention relates to a biomimetic scaffold sufficiently compact to fit through a catheter. In some embodiments the catheter is between 6 f and 34 f.

An embodiment of the invention relates to a shape memory polymer having a first polymeric network and a second polymeric network. The first polymeric network is different from the second polymeric network. In some embodiments, the first polymeric network is a biocompatible polymer-based network, and the second polymeric network is a natural oil-based network.

An embodiment of the invention relates to a scaffold body having at least two layers, wherein each of the at least two layers comprises a predetermined infill density. The two or more layers defines a network of a plurality of pores, and a distance between each of the plurality of pores varies as a function of the infill density.

An embodiment of the invention relates to a scaffold body. The scaffold body has an initial open configuration in a first environmental condition. The environmental condition is temperature.

An embodiment of the invention relates to a scaffold body having a shape memory polymer comprising a cross-linker molecule; a natural oil cross-linked to the cross-linker molecule, thereby forming a natural oil-based polymeric network; and a biocompatible polymer cross-linked to the cross-linker molecule, thereby forming a biocompatible polymer-based polymeric network. The natural oil and the biocompatible polymer are cross-linked to different regions of the cross-linker molecule.

An embodiment of the invention relates to a scaffold body having a cross-linker molecule selected from the group consisting of hexamethylene diisocyanate, poly(hexamethylene diisocyanate), isophorone diisocyanate, 1,4-phenylene diisocyanate, 1,3-phenylene diisocyanate, m-xylylene diisocyanate, tolylene-2,4-diisocyanate, or tolylene-2,6-diisocyanate.

An embodiment of the invention relates to a scaffold body having a biocompatible polymer is selected from the group consisting of polycaprolactone, polylactide, or polyethylene glycol.

An embodiment of the invention relates to a scaffold body having a biocompatible polymer is selected from the group consisting of polycaprolactone diol, polycaprolactone triol, polylactide diol, polylactide triol, polyethylene glycol diol, or polyethylene glycol triol.

An embodiment of the invention relates to a scaffold body having a natural oil is selected from the group consisting of a soybean oil based polyol, a linseed oil based polyol, a corn oil based polyol, a cottonseed oil based polyol, a palm oil based polyol, a peanut oil based polyol, a rapeseed oil based polyol, or a sunflower oil based polyol.

An embodiment of the invention relates to a scaffold body having a natural oil and a biocompatible polymer prepared at a weight ratio of the natural oil to the biocompatible polymer of between 80:20 and 20:80.

An embodiment of the invention relates to a method for producing a biomimetic scaffold body for cell growth or tissue regeneration comprising providing a template structure comprising a sacrificial scaffold, the template structure suitable for containing a shape memory polymer composition; depositing a shape memory polymer composition into the template structure; cross-linking the shape memory polymer composition; and removing the sacrificial scaffold. The scaffold body has an initial open configuration in a first environmental condition and a compact configuration in a second environmental condition. The scaffold body, when in the compact configuration, reverts to the initial open configuration in response to the first environmental condition. The scaffold body defines a network of a plurality of pores corresponding to the removed sacrificial scaffold, the plurality of pores being of a sufficient size to allow for cellular nutrient perfusion and cellular waste removal, and the scaffold body is biocompatible.

An embodiment of the invention relates to a method for producing a biomimetic scaffold body for cell growth or tissue regeneration including providing a template structure comprising a sacrificial scaffold. Providing the template structure includes creating a three-dimensional computer model of the sacrificial scaffold; and fabricating a sacrificial scaffold from a dissolvable polymer using at least one three-dimensional printing device, the sacrificial scaffold being based on the three-dimensional computer model.

An embodiment of the invention relates to a method for producing a biomimetic scaffold body for cell growth or tissue regeneration including using a dissolvable filament selected from the group consisting of polylactide, polycaprolactone, nylon, acrylonitrile butadiene styrene, styrene, polyvinyl alcohol, or polycarbonate.

An embodiment of the invention relates to a method for producing a biomimetic scaffold body for cell growth or tissue regeneration including fabricating a sacrificial scaffold. Fabricating the sacrificial scaffold includes making a graded sacrificial scaffold comprising at least two layers. Each of the at least two layers comprises a predetermined level of a percent infill density.

An embodiment of the invention relates to a method for producing a biomimetic scaffold body for cell growth or tissue regeneration including cross-linking a shape memory polymer composition. The cross-linking includes treating the shape memory polymer composition under conditions sufficient to produce a shape memory polymer comprising at least two polymeric networks. The two polymeric networks comprise at least a first polymeric network and a second polymeric network, wherein the first polymeric network is different from the second polymeric network.

An embodiment of the invention relates to a method for producing a biomimetic scaffold body for cell growth or tissue regeneration including a shape memory polymer composition comprising a cross-linker molecule; a natural oil; and a biocompatible polymer.

An embodiment of the invention relates to a method for producing a biomimetic scaffold body for cell growth or tissue regeneration including a first polymeric network comprising a biocompatible polymer-based network.

An embodiment of the invention relates to a method for producing a biomimetic scaffold body for cell growth or tissue regeneration including a second polymeric network comprises a natural oil-based network.

An embodiment of the invention relates to a method for producing a biomimetic scaffold body for cell growth or tissue regeneration including using a cross-linker molecule selected from the group consisting of hexamethylene diisocyanate, poly(hexamethylene diisocyanate), isophorone diisocyanate, 1,4-phenylene diisocyanate, 1,3-phenylene diisocyanate, m-xylylene diisocyanate, tolylene-2,4-diisocyanate, or tolylene-2,6-diisocyanate.

An embodiment of the invention relates to a method for producing a biomimetic scaffold body for cell growth or tissue regeneration including using a biocompatible polymer selected from the group consisting of polycaprolactone, polylactide, or polyethylene glycol.

An embodiment of the invention relates to a method for producing a biomimetic scaffold body for cell growth or tissue regeneration including a biocompatible polymer selected from the group consisting of polycaprolactone diol, polycaprolactone triol, polylactide diol, polylactide triol, polyethylene glycol diol, polyethylene glycol triol.

An embodiment of the invention relates to a method for producing a biomimetic scaffold body for cell growth or tissue regeneration including a natural oil selected from the group consisting of a castor oil, a soybean oil based polyol, a linseed oil based polyol, a corn oil based polyol, a cottonseed oil based polyol, a palm oil based polyol, a peanut oil based polyol, a rapeseed oil based polyol, or a sunflower oil based polyol.

An embodiment of the invention relates to a method for producing a biomimetic scaffold body for cell growth or tissue regeneration including a natural oil and a biocompatible polymer present at a weight ratio of the natural oil to the biocompatible polymer of between 80:20 and 20:80.

An embodiment of the invention relates to a shape memory polymer composition having a cross-linker molecule comprising at least two isocyanate groups; a natural oil comprising a hydroxyl group cross-linked to at least one of the at least two isocyanate groups, thereby forming a natural oil-based polymeric network; and a biocompatible polymer comprising a hydroxyl group cross-linked to at least one of the at least two isocyanate groups, thereby forming a biocompatible polymer-based polymeric network. The natural oil and the biocompatible polymer are cross-linked to different isocyanate groups.

An embodiment of the invention relates to a shape memory polymer composition having at least two isocyanate groups of on a cross-linker cross-linked with either a hydroxyl group of a natural oil or a hydroxyl group of a biocompatible polymer.

An embodiment of the invention relates to a shape memory polymer composition having hexamethylene diisocyanate, poly(hexamethylene diisocyanate), isophorone diisocyanate, 1,4-phenylene diisocyanate, 1,3-phenylene diisocyanate, m-xylylene diisocyanate, tolylene-2,4-diisocyanate, or tolylene-2,6-diisocyanate.

An embodiment of the invention relates to a shape memory polymer composition having a cross-linker molecule having at least three isocyanate groups, and wherein at least two of the isocyanate groups are cross-linked with at least two hydroxyl groups of a biocompatible polymer.

An embodiment of the invention relates to a shape memory polymer composition having a cross-linker molecule having at least three isocyanate groups. At least two of the isocyanate groups are cross-linked with at least two hydroxyl groups of a natural oil.

An embodiment of the invention relates to a shape memory polymer composition having a biocompatible polymer selected from the group consisting of polycaprolactone, polylactide, or polyethylene glycol.

An embodiment of the invention relates to a shape memory polymer composition having a biocompatible polymer is selected from the group consisting of polycaprolactone diol, polycaprolactone triol, polylactide diol, polylactide triol, polyethylene glycol diol, polyethylene glycol triol.

An embodiment of the invention relates to a shape memory polymer composition having a natural oil is selected from the group consisting of a castor oil, a soybean oil based polyol, a linseed oil based polyol, a corn oil based polyol, a cottonseed oil based polyol, a palm oil based polyol, a peanut oil based polyol, a rapeseed oil based polyol, or a sunflower oil based polyol.

An embodiment of the invention relates to a shape memory polymer composition having a weight ratio of a natural oil to a biocompatible polymer of between 80:20 and 20:80.

An embodiment of the invention relates to a shape memory polymer composition having a biocompatible polymer having an average molecular weight (Mn) of at most 10000.

An embodiment of the invention relates to a shape memory polymer composition having a biocompatible polymer having an average molecular weight (Mn) of between 300 and 900.

An embodiment of the invention relates to a method of forming a shape memory polymer including: preparing a shape memory polymer composition comprising a cross-linker molecule having at least two isocyanate groups; a natural oil having comprising a hydroxyl group; and a biocompatible polymer comprising a hydroxyl group. Cross-linking the shape memory polymer composition results in a hydroxyl group of the natural oil is cross-linked to at least one of the isocyanate groups and a hydroxyl group of the biocompatible polymer is cross-linked to at least one of the isocyanate groups. The natural oil and the biocompatible polymer are cross-linked to different isocyanate groups. The crosslinking of the natural oil to the cross-linker forms a natural oil-based polymeric network, and the cross-linking of the biocompatible polymer to the cross-linker forms a biocompatible polymer-based network.

An embodiment of the invention relates to a method of forming a shape memory polymer including cross-linking comprising heat a composition to a first temperature for a time sufficient to promote cross-linking of a cross-linker molecule, a natural oil, a the biocompatible polymer; and cooling the composition to a second temperature following the heating. The second temperature is lower than the first temperature.

An embodiment of the invention relates to a method of forming a shape memory polymer including heating a composition to a third temperature before cooling. The third temperature is greater than a first temperature.

An embodiment of the invention relates to a method of forming a shape memory polymer including a cross-linker molecule selected from the group consisting of hexamethylene diisocyanate, poly(hexamethylene diisocyanate), isophorone diisocyanate, 1,4-phenylene diisocyanate, 1,3-phenylene diisocyanate, m-xylylene diisocyanate, tolylene-2,4-diisocyanate, or tolylene-2,6-diisocyanate.

An embodiment of the invention relates to a method of forming a shape memory polymer including a biocompatible polymer selected from the group consisting of polycaprolactone, polylactide, or polyethylene glycol.

An embodiment of the invention relates to a method of forming a shape memory polymer including a biocompatible polymer is selected from the group consisting of polycaprolactone diol, polycaprolactone triol, polylactide diol, polylactide triol, polyethylene glycol diol, polyethylene glycol triol.

An embodiment of the invention relates to a method of forming a shape memory polymer including a natural oil is selected from the group consisting of a castor oil, a soybean oil based polyol, a linseed oil based polyol, a corn oil based polyol, a cottonseed oil based polyol, a palm oil based polyol, a peanut oil based polyol, a rapeseed oil based polyol, or a sunflower oil based polyol.

An embodiment of the invention relates to a method of forming a shape memory polymer including a natural oil and a biocompatible polymer prepared at a weight ratio of the natural oil to the biocompatible polymer of between 80:20 and 20:80.

An embodiment of the invention relates to a method of forming a shape memory polymer including a biocompatible polymer having an average molecular weight (Mn) of between 300 and 900.

An embodiment of the invention relates to a biomimetic scaffold for cell growth or tissue regeneration having a scaffold body including a shape memory polymer. The scaffold body has an initial open configuration in a first environmental condition and a compact configuration in a second environmental condition. The scaffold body, when in the compact configuration, reverts to the initial open configuration in response to being exposed to the first environmental condition. The scaffold body defines a network of a plurality of pores, the plurality of pores being of a sufficient size to allow for cellular nutrient perfusion and cellular waste removal, and the scaffold body is biocompatible.

FIG. 1 is a schematic illustration of a biomimetic scaffold 100 for cell growth or tissue regeneration according to an embodiment of the current invention. The biomimetic scaffold 100 includes a scaffold body 102 that includes a shape memory polymer 104. The scaffold body has an initial open configuration 106 in a first environmental condition and a compact configuration 108 in a second environmental condition. The scaffold body, when in the compact configuration, reverts to the initial open configuration in response to being exposed to the first environmental condition. The scaffold body defines a network of a plurality of pores, the plurality of pores being of a sufficient size to allow for cellular nutrient perfusion and cellular waste removal, and the scaffold body is biocompatible.

Definitions

The term "4D printing" refers to a process for fabricating a device or structure that can adopt multiple pre-determined configurations in response to environmental conditions. In some examples, the shape transformation of the fabricated device occurs when implanted minimally-invasively. The "4D effect," or ability of a device or structure to adopt multiple pre-determined configurations in response to environmental conditions, is realized by programmed action of a shape memory polymer. The device can take on at least two conformations, with one "open" confirmation occurring in response a first environmental condition and a second "compact" conformation occurring in response to a second environmental condition. In some examples, 4D printing involves 3D printing of shape memory scaffolds.

The terms "shape memory polymer," shape memory co-polymer," "smart polymer," or "smart co-polymer" are used interchangeably throughout and generally refer to a molecule composed of many repeated subunits that has the ability to take on different configurations in different environments with a change in environment resulting in a change in configuration. Such polymers can be made of multiple individual molecules or polymers cross-linked together to form a co-polymer with distinct networks made of the individual molecules or polymers. Such polymers can also be naturally-derived, synthetically derived, or a combination of naturally-derived and synthetically derived molecules or polymers. In some non-limiting examples, such polymers are able to quickly revert to an initial configuration following distortion and exhibit greater than 92% shape fixing at −18 or 0° C. and full shape recovery at physiological temperature. Also, in non-limiting examples, these polymers are suitable for physiological temperature triggered shape change.

The term "biocompatible" refers to a product, composition or molecule that is non-toxic or is minimally toxic to tissues and/or cells and is generally not considered antigenic. In addition, a biocompatible product, composition or molecule does not adversely affect the biological processes of a cell and/or tissue.

The term "biomimetic" refers to a product, composition or molecule that in general mimics an element of nature. In some examples, the biomimetic product, composition or molecule mimics natural tissues or aspects of natural tissues. Such a product, composition or molecule is non-toxic or is minimally toxic to tissues and/or cells and is generally not considered antigenic. In addition, such a product, composition or molecule does not adversely affect the biological processes of a cell and/or tissue.

The term "sacrificial template" refers to a structure that is employed during the fabrication of a product, but is removed prior to completing fabrication of the product. Such a template can be made of, for example, a sacrificial filament. In such examples, the sacrificial filament is of sufficient composition and integrity to form the sacrificial template when in use, but can be readily removed from the product prior to completion of the fabrication process. Removing can be, but is not limited to dissolving, melting, chemically etching, etc. The sacrificial template can be configured to take on a variety of shapes as needed. An example of such a shape can be a scaffold of a predetermined design.

In some embodiments, the shape memory polymer comprises a natural oil or a synthetic oil. In some embodiments, the natural or synthetic oil has at least one hydroxyl group. In some embodiments, the natural or synthetic oil is treated to add a hydroxyl group to it. One of ordinary skill in the art would readily appreciate how to treat a natural or synthetic oil so that a hydroxyl group is added to it.

For instance, vegetable oil based polyols can be synthesized by the following method: Vegetable oil (100 g) and formic acid (50 mL) are mixed in a reactor at 50° C. with a stirring speed of 300 rpm. Then, 120 mL hydrogen peroxide is added dropwise for more than 2 h. The reaction is allowed for 6 h at 50° C. The reaction mixture is cooled down to 25° C. The epoxidized vegetable oil is extracted with dichloromethane, and washed with water to remove unreacted hydrogen peroxide and formic acid. The epoxidized vegetable oil is obtained after removing of the dichloromethane. The epoxy groups in the epoxidized vegetable oil are then opened by methanol to form vegetable oil based polyol. Briefly, epoxidized vegetable oil (10 g) is mixed with p-toluene sulfonic acid (1-5% of epoxidized vegetable oil) and 100 mL methanol in a reactor. The mixture is refluxed with stirring at 75° C. for 10 h. The vegetable oil based polyol is extracted with dichloromethane, and washed with water to remove p-toluene sulfonic acid. The vegetable oil based polyol is obtained after removing of the dichloromethane and unreacted methanol. It is within the skill level of one of ordinary skill in the art to synthesize other hydroxyl-group containing oils from a natural or synthetic oil.

The following example describe some embodiments and some applications in more detail. However, the broad concepts of the current invention are not limited to the particular example.

Example

Abstract

An objective of this study is to 4D print novel biomimetic gradient tissue scaffolds with highly biocompatible naturally derived smart polymers. The term "4D printing" refers to the inherent smart shape transformation of fabricated constructs when implanted minimally-invasively for seamless and dynamic integration. For this purpose, a series of novel shape memory polymers with excellent biocompatibility and tunable shape changing effects were synthesized and cured in the presence of 3D printed sacrificial molds which were subsequently dissolved to create controllable and graded porosity within the scaffold. Surface morphology, thermal, mechanical and biocompatible properties as well as shape memory effects of the synthesized smart polymers and resultant porous scaffolds were characterized. Fourier transform infrared spectroscopy and gel content analysis confirmed the formation of chemical cross-linking by reacting polycaprolactone triol and castor oil with multi-isocyanate groups. Differential scanning calorimetry revealed an adjustable glass transition temperature in a range from −8 to 35° C. Uniaxial compression testing indicates that the obtained polymers have similar compressive modulus to polycaprolactone forming a highly crosslinked interpenetrating polymeric networks. Shape memory tests revealed that the smart polymers display finely tunable recovery speed and exhibit greater than 92% shape fixing at −18 or 0° C. and full shape recovery at physiological temperature. Scanning electron microscopy analysis of fabricated scaffolds revealed a graded microporous structure which mimics the non-uniform distribution of porosity found within natural tissues. With polycaprolactone serving as a control, human bone marrow-derived mesenchymal stem cell adhesion, proliferation and differentiation greatly increased on our novel smart polymers. The current work will significantly advance the future design and development of novel and functional biomedical scaffolds with advanced 4D printing technology and highly biocompatible smart biomaterials.

Introduction

Tissue engineered scaffolds are commonly defined as three dimensional (3D) porous structures composed of biocompatible materials which perform multiple functions such as the promotion of cell adhesion and proliferation as well as directed tissue repair and regeneration. (1) In order to achieve an ideal tissue engineered scaffold, material selection and scaffold fabrication technique are extremely important. Various materials with different physicochemical properties have been investigated for use in biomedical scaffolds, including metals,(2) ceramics,(3) polymers(4-7) and composites(8). Among these materials, shape memory polymers have attracted particular interest due to the potential for facile and minimally invasive surgical delivery with in situ shape activation for considerable reduction of trauma and significant improvement of patient comfort.(9, 10) Additionally, seamless integration between the scaffold and defect would be better facilitated and addressed through the inherent shape memory effect.(9)

Several methods for 3D porous scaffold fabrication have been explored including: solid freeform fabrication,(11) electrospinning,(12) thermally induced phase separation, (13) solvent casting/particle leaching,(14) microsphere sintering(15) and scaffold coating(16). Amongst these fabrication techniques, 3D printing has garnered greater attention due to its excellent control of scaffold shape and interconnected porosity.(17-19) Briefly, scaffolds are printed layer-by-layer based on pre-designed computer-aided-design (CAD) files.(19) Axial movement of the printing head is precisely controlled allowing for accurate and precise pore size, shape, and interconnectivity which can be extended towards the fabrication of patient-specific defects.

Building upon 3D printing technologies, 4D printing is an emerging new concept which refers to the ability of 3D printed objects to change form and function after fabrication, thereby offering additional capabilities and performance-driven applications.(20) For example, hydrophilic materials have been utilized to 4D fabricate self-evolving structures which perform geometric folding, curling, expansion and various other programmed shape changes after submersion in water;(20) active composite materials are prepared by printing glassy shape memory polymer fibers in an elastomeric matrix and the 4D effect is realized by programmed action of the shape memory fibers(21). 3D printing of shape memory biomedical scaffolds will have great potential for regenerative medicine in view of the combined advantages of 3D printing and the time-dependent shape memory effect. However, to the best of our knowledge, smart biomedical scaffolds fabricated by 4D printing with shape memory polymers have not been reported.

Therefore, in the current study, biomimetic hierarchical scaffolds were 4D fabricated from highly biocompatible smart polymers to serve as dynamic scaffolds for regenerative medicine as schematically shown in FIG. 1. In comparison to common biomedical scaffolds which mostly have uniformly distributed porosity, 3D printing was utilized to achieve a gradient distribution of porosity from the periphery to the center of the construct to mimic natural tissues such as bone. The materials used in the study are smart biopolymers which were developed in our lab exhibiting excellent shape memory effects and shape recovery at physiological temperature. The biopolymers have also shown extraordinary biocompatibility with excellent attachment, proliferation and differentiation of mesenchymal stem cells. The results of this research have shed a light on the future design and development of novel and functional biomedical scaffolds with advanced 4D printing technology and highly biocompatible smart biopolymers.

Materials and Methods

Synthesis of Smart Polymer

Predetermined amounts of castor oil were mixed with polycaprolactone triol (number average molecular weight of 300 (Ptriol300) or 900 (Ptriol900)) and a cross-linker (either hexamethylene diisocyanate (HD) or poly(hexamethylene diisocyanate) (PH)) homogeneously in a glass beaker at room temperature then heated to 60° C. The mixture was then poured into a polystyrene box and degassed to remove air bubbles. The plastic box was covered with a lid and put into a 60° C. oven. The curing process was allowed to proceed for 48 h and the temperature was then increased to 70° C. for an additional 24 h. The polymers were removed and allowed to sit at room temperature for a minimum of 24 h before analysis. Samples were coded according to the ratio of castor oil to Ptriol, Ptriol molecular weight, and the cross-linker type. For example, sample C80P300PH was composed of an 80:20 weight ratio of castor oil to Ptriol300 with PH serving as the cross-linker. In total, 22 samples were synthesized.

Porous Scaffold Fabrication

Interconnected porous scaffolds were designed in Rhinoceros 3D (McNeel North America, Seattle, Wash.), prepared for 3D printing using the open source software package Slic3r, and 3D printed via a Solidoodle Workbench Apprentice 3D printer (Solidoodle, Brooklyn, N.Y.). Poly(lactic acid) (PLA) molds were printed with the following parameters; filament diameter: 1.75 mm; extrusion multiplier: 1; nozzle diameter: 250 µm; extruder temperature: 175° C.; bed temperature: 75° C.; layer height: 0.3 mm; and solid infill. In order to achieve a graded structure, the infill density was changed. Specifically, 25% was used for the $1^{st}$ and $2^{nd}$ layer; 30% for the $3^{rd}$ and $4^{th}$ layers; 35% for the $5^{th}$ and $6^{th}$ layers; and 40% for the $7^{th}$ and $8^{th}$ layers. After printing, the PLA structure was filled with the heated reaction mixture for synthesizing smart polymers. The same curing process was employed as described previously. The graded porous scaffold was obtained after the PLA was removed by dissolving with dichloromethane and acetone sequentially.

Polymer and Scaffold Characterization

A FTIR spectrometer (Nicolet Series II Magna-IR System 750, Nicolet Instrument Inc.) equipped with a horizontal germanium attenuated total reflectance accessory (ATR-FTIR) was used to evaluate all samples. The scan range used was 600 to 4000 cm$^{-1}$ with a resolution of 4 cm$^{-1}$.

Sol-gel analysis was performed according to a reported method with slight modification.(22) Briefly, 0.5 g sample was placed in 20 mL acetone and allowed swell for a day at room temperature, and another 48 h at 50° C. The swollen gel was removed and dried at 60° C. for 48 h. The gel content was determined as the weight of the dried sample divided by the total weight of the original sample.

Surface wettability of test specimens was measured using a contact angle analyzer (DSA4; Kruss). Approximately 3 µL of ultrapure $H_2O$ was deposited on the samples' surface and recorded. Static contact angle measurements were obtained from the first image of every recording. All experiments were conducted in ambient conditions and repeated five times per sample.

Surface morphology characterization of the smart polymer and porous structure of fabricated scaffolds were observed via a focused ion beam operating in scanning electron microscopy (SEM) mode (Zeiss NVision 40 FIB) under an accelerating voltage of 1-2 kV. The scaffold was cut with a scalpel to observe the internal interconnected pores and gold sputter-coated prior to imaging.

The glass transition temperature ($T_g$s) of synthesized polymers was measured with a multi-cell differential scanning calorimeter (MC DSC) from TA Instruments (New Castle, Del.) at a programmed ramp rate of 1° C./min. The sample was first heated from 25 to 150° C. and held at 150° C. for 1 min. Next, the sample was cooled from 150 to −30° C., and held at −30° C. for 1 min. A second cycle was conducted: heating from −30 to 150° C., holding 1 min and decreasing from 150 to −30° C. where results from this second cycle were used to determine the $T_g$s.

Uniaxial compression tests were conducted using a uniaxial mechanical tester from MTS Systems Corporation (Eden Prairie, Minn.). Briefly, a flat 2 cm diameter platen attached to a 100 N load cell was advanced upon the sample (8 mm diameter cylinder, 2 mm high) at a test speed of 10 mm/min and strain endpoint of 5 mm/mm. Data were taken using LabView (National Instruments Corporation, Austin, Tex.) and Young's modulus determined by the linear elastic region.

Shape memory tests were conducted according to a reported method with slight modification.(23) The polymer specimens were cut into rectangular strips measuring 75×10×2 mm. The edges of the strips were stained with black dye for increased optical contrast. The strips were folded 180° at 37° C. into a "U" shape with a mold possessing an inner radius of 10 mm and kept at this temperature for 10 min. The samples were then cooled down immediately to a predetermined temperature (0 or −18° C.) and maintained at temperature for an additional 10 min. The mold was removed and the test strips were kept at temperature for an additional 10 min. The fixed angle of the specimen was determined and recorded as $\theta_{fixed}$. The strips were then immersed in 37° C. phosphate buffered saline (PBS) immediately to recover the permanent shape. The time evolution of the specimen angle was determined by image processing and plotted v.s. time to quantitatively evaluate the transition speed. The final angle of the specimen was determined and recorded as $\theta_{final}$. Shape fixity ($R_f$) and shape recovery (Rr) were calculated by the following equations:

$$R_f = \theta_{fixed}/180 \times 100\% \quad (I)$$

$$R_r = (\theta_{fixed} - \theta_{final})/\theta_{fixed} \times 100\% \quad (II)$$

Human Bone Marrow Mesenchymal Stem Cell (MSC) Biocompatibility

Primary human bone marrow MSCs were obtained from healthy consenting donors at the Texas A&M Health Science Center, Institute for Regenerative Medicine. MSCs (passage No. 3-6) were cultured in complete media composed of alpha minimum essential medium (Gibco) supplemented with 16.5% fetal bovine serum (FBS) (Atlanta Biologicals), 1% (v/v) l-glutamine (Invitrogen), and 1% penicillin:streptomycin solution (Invitrogen) and cultured under standard cell culture conditions (37° C., a humidified, 5% $CO_2$/95% air environment).

For MSC adhesion studies, the polymer test samples were cut into 8 mm diameter specimens. MSCs were seeded at a cell density of 50,000 cells/specimen and cultured under standard cell culture conditions for 4 h. The specimens were then washed three times with PBS to remove nonadherent cells. Attached cells were lifted with trypsin-ethylenediaminetetraacetic acid and quantified with CellTiter 96" Aqueous Non-Radioactive Cell Proliferation Assay and analyzed spectrophotometrically using a Thermo Scientific Multiskan GO Spectrophotometer at 490 nm.

For proliferation studies, MSCs were seeded at a density of 10,000 cells/scaffold and cultured for 1, 3, and 5 days, respectively. Media was exchanged every other day and adhered cells were quantified as previously described. In addition, confocal microscopy was used to qualitatively examine MSC growth and spreading morphology. At each time point, samples were washed twice with PBS, fixed with 10% formalin and permeabilized in 0.1% Triton X-100. After rinsing with PBS, cells were stained with Texas red fluorescent dye (to stain the cells' cytoskeleton) for 1 h and then DAPI blue fluorescent dye (to stain the cells' nuclei) for 15 min and imaged on a Zeiss LSM 710 confocal microscope.

For MSC osteogenic differentiation, MSCs were seeded at a density of 200,000 cells/$cm^2$. Osteogenic differentiation media [DMEM supplemented with 10% FBS, 1% Penicillin-Streptomycin, 50 mg/mL 1-ascorbate acid (Sigma), and 10 mM b-glycerophosphate (Sigma)] was used to culture the cells for 7 and 14 days. At each predetermined time point, the samples were moved into a new well-plate and rinsed with 50 mM Tris-buffered saline. MSCs were lysed using distilled water and three freeze-thaw cycles to disrupt the cell membrane and allow for intracellular and membrane-bound protein release.(24) The biological activity of alkaline phosphatase (ALP) in the disrupted solution was measured with a QuantiChrom™ Alkaline Phosphatase Assay Kit (BioAssay Systems, Hayward, Calif.). The enzyme activity of ALP was set in relation to the total concentration of protein in solution which was determined with a bicinchoninic acid assay (Micro BCA Protein Assay Kit, Thermo Scientific, Rockford, Ill.) to calculate the ALP specific activity (mmol/mg/h). Calcium deposition on different materials was measured using a calcium reagent kit (Pointe Scientific Inc.). Briefly, the material scaffold was immersed in a 0.6N hydrogen chloride (HCl) solution at 37° C. for 24 h. By reacting with o-cresolphthalein complex one, the calcium in the acidic supernatant was qunantified. The absorbance at 570 nm was determined, and the calcium was calculated by standard curves of known calcium concentrations.

Statistical Analysis

All data are expressed as mean±standard deviation. The statistical significance was analyzed by a one-way ANOVA test followed by using Tukey's pair-wise comparison of the means. A significance level of p<0.05 was used for all analyses.

Results

Synthesis and Characterization of Smart Polymer

Figure 2:
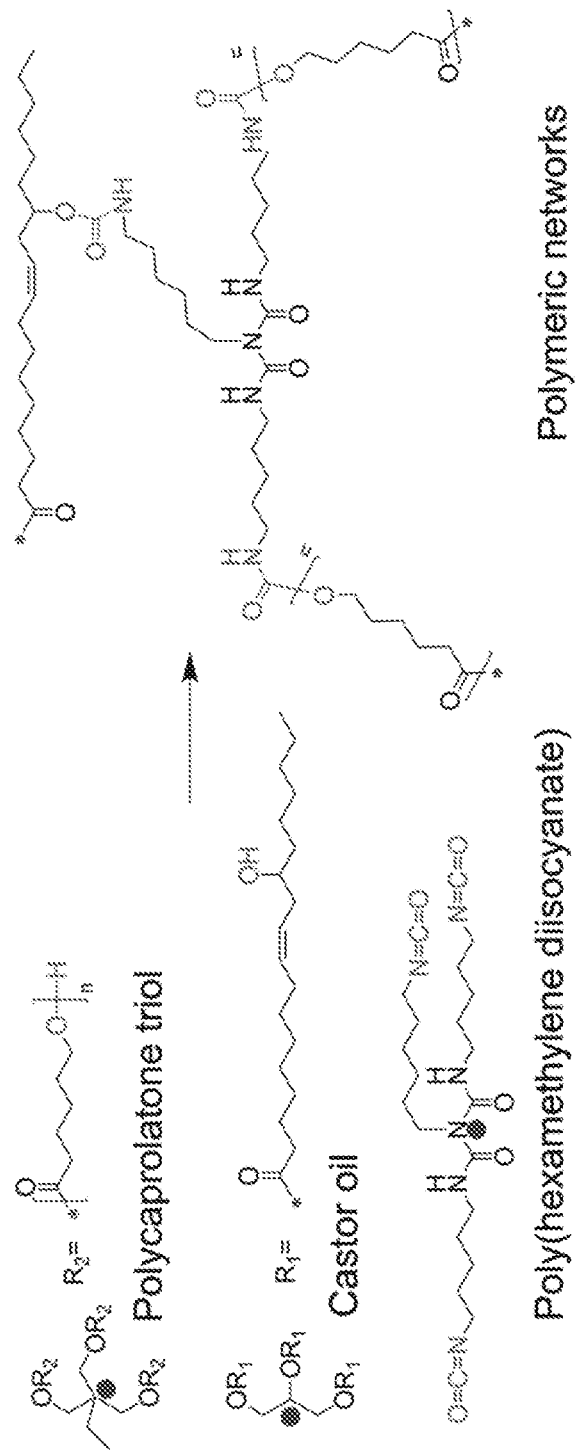
FIG. 2 is a schematic showing a reaction mechanism for synthesis of a shape memory polymer.

The reaction mechanism is schematically shown in FIG. 2 and described below.

In FIG. 2, the biocompatible polymer is Polycaprolactone triol (Ptriol). It is represented by the Formula (I):

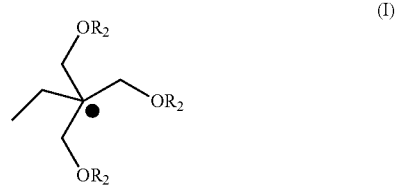

where $R_2$ is

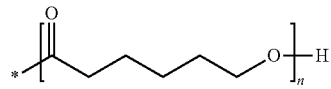

The natural oil is castor oil. It is represented by the Formula (II):

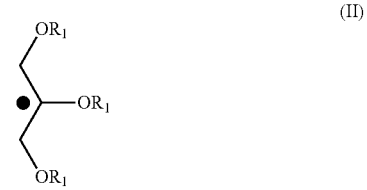

where R1 is:

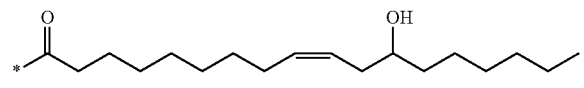 [SMILES: *C(=O)CCCCCCC/C=C\CC(O)CCCCCC]

The cross-linker is Poly(hexamethylene diisocyantae) (PH). It is represented by the Formula (III):

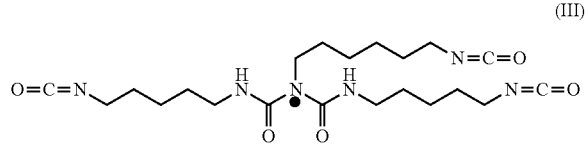

The hydroxyl groups in Ptriol and castor oil additively react with isocyanate groups in hexamethylene diisocyantae (HD) or PH to form urethane bonds. Theoretically, there are two polymeric networks (Ptriol and castor oil based networks, respectively) and three types of cross-linking points (the dots in FIG. 2) in the resultant polymeric networks, which is expected to generate excellent shape recovery effects with widely tunable properties. By varying the ratio of components, a series of smart polymers have been prepared with all formulations presented in Table 1. For all synthesized samples, the molar ratio of hydroxyl group to isocyanate group is kept constant at 1:1.05. The compatibility amongst the constituents plays a key role in preparing the polymeric networks. Most synthesized samples formed transparent films with Ptriol300HD and C20P300HD the exceptions due to immiscibility of the reagents which yielded a highly viscous mixture with noticeable agglomerations. All other samples were screened for their shape memory effects. For this purpose, the samples were folded into a "U" shape at 37° C. and their shape fixities determined at 0 or −18° C. If the $R_f$ is <90%, the sample is considered as having no shape fixity effect. As indicated in Table 1, five samples were found to possess a shape fixing effect and further investigated.

Figures 3A, 3B, 3C:
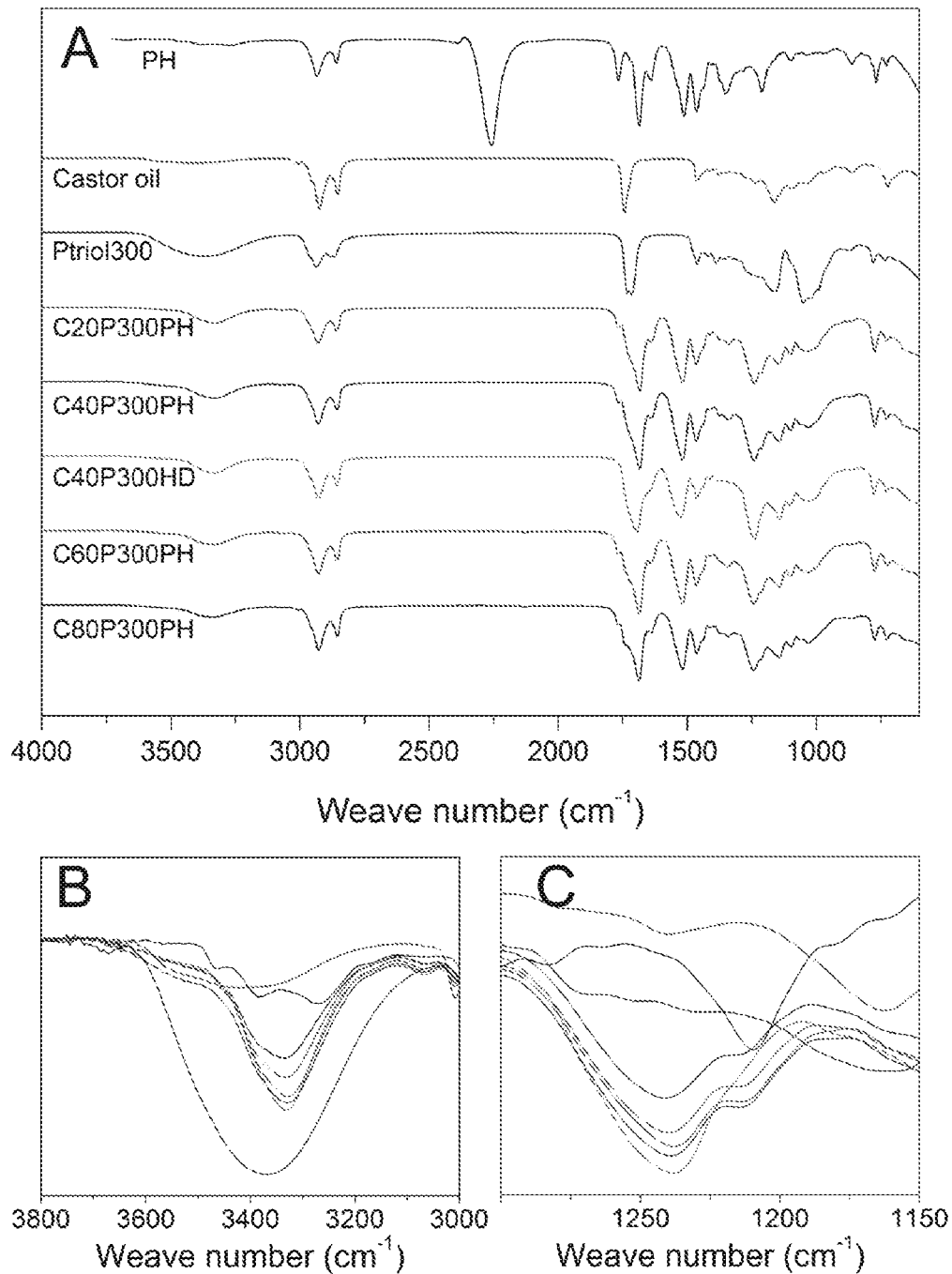
FIG. 3A-3C are graphs showing Fourier Transform Infrared Spectroscopy (FTIR) spectra of five smart polymers when compared to Poly(hexamethylene diisocyante) (PH), castor oil and Polycaprolactone Triol (Ptriol) 300.

The formation of the urethane bonds in the five samples exhibiting shape memory effect was confirmed by FTIR analysis as shown in FIG. 3. The signal at 2256 cm$^{-1}$ in PH corresponds to the isocyanate group and is absent in the smart polymers thus implying complete consumption of isocyanates (FIG. 3A). The signal at 3368 cm$^{-1}$ in Ptriol300 is attributed to the replacement of hydroxyl groups by the amide N—H stretching signal at 3329 cm$^{-1}$ in smart polymers as shown in FIG. 3B, indicating the reaction of hydroxyl groups and formation of urethane bonds. The presence of a characteristic polyurethane peak in the amide I region 1650-1760 cm$^{-1}$ corresponding to C=O stretching vibration is not clearly visible in the synthesized smart polymers due to the signal overlaps with the neighboring C=O stretching vibration in PH. However, the formation of urethane bonds was further confirmed by the presence of a peak at 1238 cm$^{-1}$ due to C—N stretching where this peak is absent in castor oil, Ptriol300 and PH, as shown in FIG. 3C.

Figures 4A, 4B, 4C, 4D:
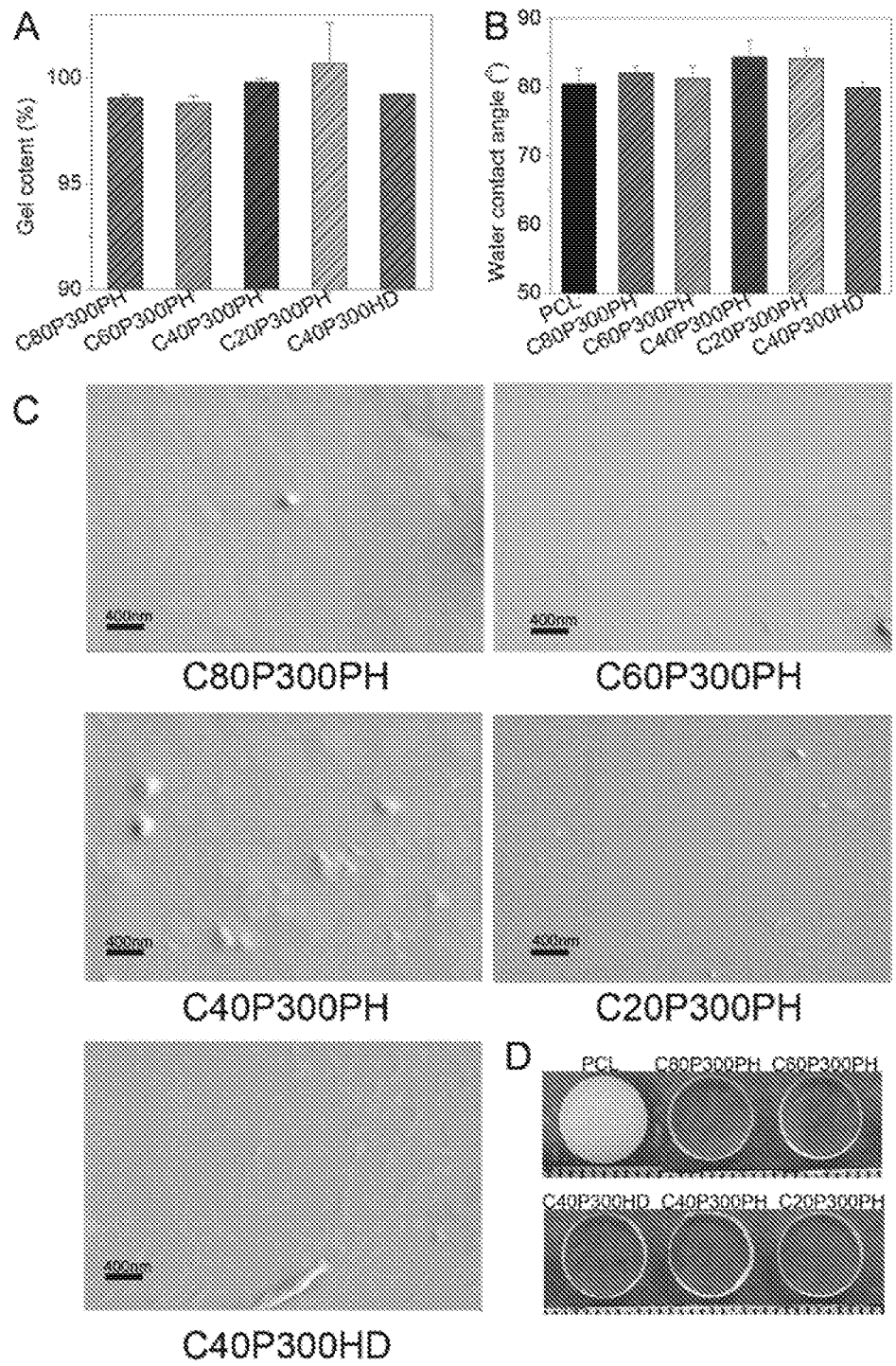
FIG. 4A is a graph showing Gel content of example scaffolds; 4B is a graph showing water contact angle of example scaffolds; 4C shows Scanning Electron Microscopy (SEM) images of example scaffolds; 4D shows photo images example scaffolds.

The gel content of synthesized smart polymers is shown in FIG. 4A indicating that the polymers are fully cross-linked with gel contents greater than 95%. Contact angle analysis is shown in FIG. 4B with no statistical difference observed between the smart polymers and polycaprolactone (PCL) control. Surface morphology was evaluated via SEM and is shown in FIG. 4C. No noticeable surface topography changes were observed suggesting that the smart polymers do not exhibit specific surface structures. Optical clarity can be seen in FIG. 4D where all five smart polymers are transparent when compared to PCL.

Figures 5A, 5B, 5C:
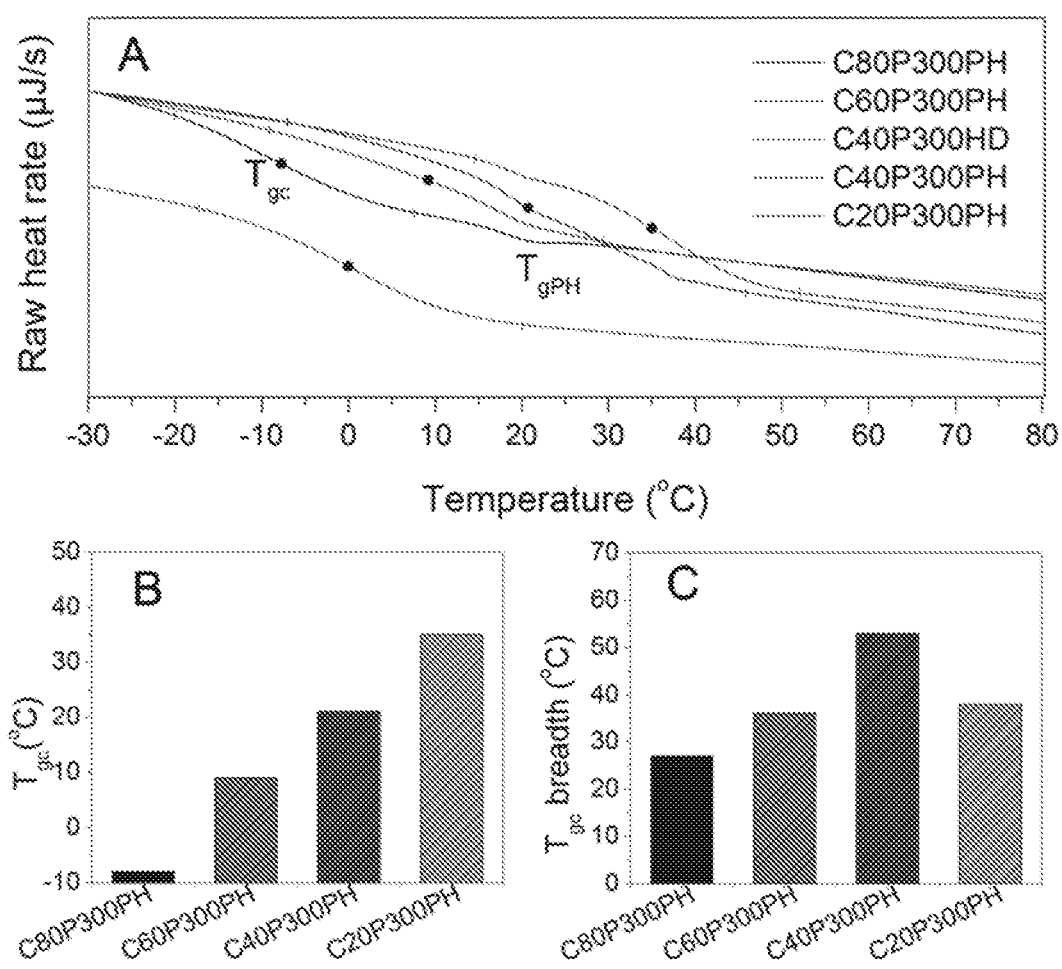
FIG. 5A-5C show graphs showing Differential Scanning calorimetry (DSC) curves synthesized example smart polymers.

The $T_g$s of smart polymers was determined by DSC and results are shown in FIG. 5. A $T_g$ of 21° C. was observed in all the samples with PH as cross-linker while no glass transition was observed at this temperature for sample C40P300HD. Therefore, this glass transition ($T_{gPH}$) is assumed to be a function of the PH chains where $T_{gPH}$ is not significantly affected by the sample composition. In contrast, the $T_g$ from the incorporation of castor oil and Ptriol300 ($T_{gc}$) is proportional to castor oil content. As shown in FIGS. 5A and 5B, the $T_{gc}$ shifts from −8 to 35° C. when the ratio of castor oil to Ptriol300 decreases from 80:20 to 20:80 which implies that these smart polymers are suitable for physiological temperature trigged shape change. No other glass transition is clearly visible except $T_{gPH}$ and $T_{gc}$, implying that castor oil and Ptriol300 are highly miscible and well distributed within the samples. $T_{gc}$ is clearly distinct from $T_{gPH}$ in sample C80P300PH which indicates a phase separation between PH and other components. This separation is not distinguishable amongst all other samples as noted in sample C40P300PH where an overlap of $T_{gc}$ and $T_{gPH}$ is observed. The $T_{gc}$ breadth (the temperature range between $T_{gc}$ onset and offset) is dependent upon the castor oil content. As shown in FIGS. 5A and 5C, sample C40P300PH has the greatest $T_{gc}$ breadth.

TABLE 1

The constitutions of the smart polymers

| Sample code | castor oil/g | Ptriol300/g | Ptriol900/g | HD/g | PH/g | castor oil:Ptriol*[1] | SME*[2] |
|---|---|---|---|---|---|---|---|
| Castor100HD | 12.0676 | | | 2.9324 | | 100:0 | |
| Castor100PH | 9.9338 | | | | 5.0662 | 100:0 | |
| Ptriol900HD | | | 11.5186 | 3.4814 | | 0:100 | |
| Ptriol900PH | | | 9.1781 | | 5.8219 | 0:100 | |
| Ptriol300HD | | 7.8669 | | 7.1331 | | 0:100 | |
| Ptriol300PH | | 5.1670 | | | 9.8329 | 0:100 | |
| C80P300HD | 8.6912 | 2.1728 | | 4.1359 | | 80:20 | |
| C80P300PH | 6.7092 | 1.6773 | | | 6.6136 | 82:20 | Yes |
| C80P900HD | 9.5253 | | 2.3813 | 3.0933 | | 80:20 | |
| C80P900PH | 7.8181 | | 1.9545 | | 5.2274 | 80:20 | |
| C60P300HD | 5.9662 | 3.9775 | | 5.0563 | | 60:40 | |
| C60P300PH | 4.3537 | 2.9025 | | | 7.7438 | 60:40 | Yes |
| C60P900HD | 7.1034 | | 4.7356 | 3.161 | | 60:40 | |
| C60P900PH | 5.7703 | | 3.8469 | | 5.3828 | 60:40 | |
| C40P300HD | 3.6559 | 5.4838 | | 5.8603 | | 40:60 | Yes |
| C40P300PH | 2.5578 | 3.8366 | | | 8.6056 | 40:60 | Yes |
| C40P900HD | 4.6930 | | 7.0395 | 3.2675 | | 40:60 | |
| C40P900PH | 3.7864 | | 5.6797 | | 5.5339 | 40:60 | |
| C20P300HD | 1.6911 | 6.7644 | | 6.5445 | | 20:80 | |
| C20P300PH | 1.1431 | 4.5725 | | | 9.2844 | 20:80 | Yes |
| C20P900HD | 2.3249 | | 9.2994 | 3.3757 | | 20:80 | |
| C20P900PH | 1.8640 | | 7.4562 | | 5.6798 | 20:80 | |

*[1]Weight ratio of castor oil to Ptriol
*[2]Shape memory effect (SME)

Figure 6:
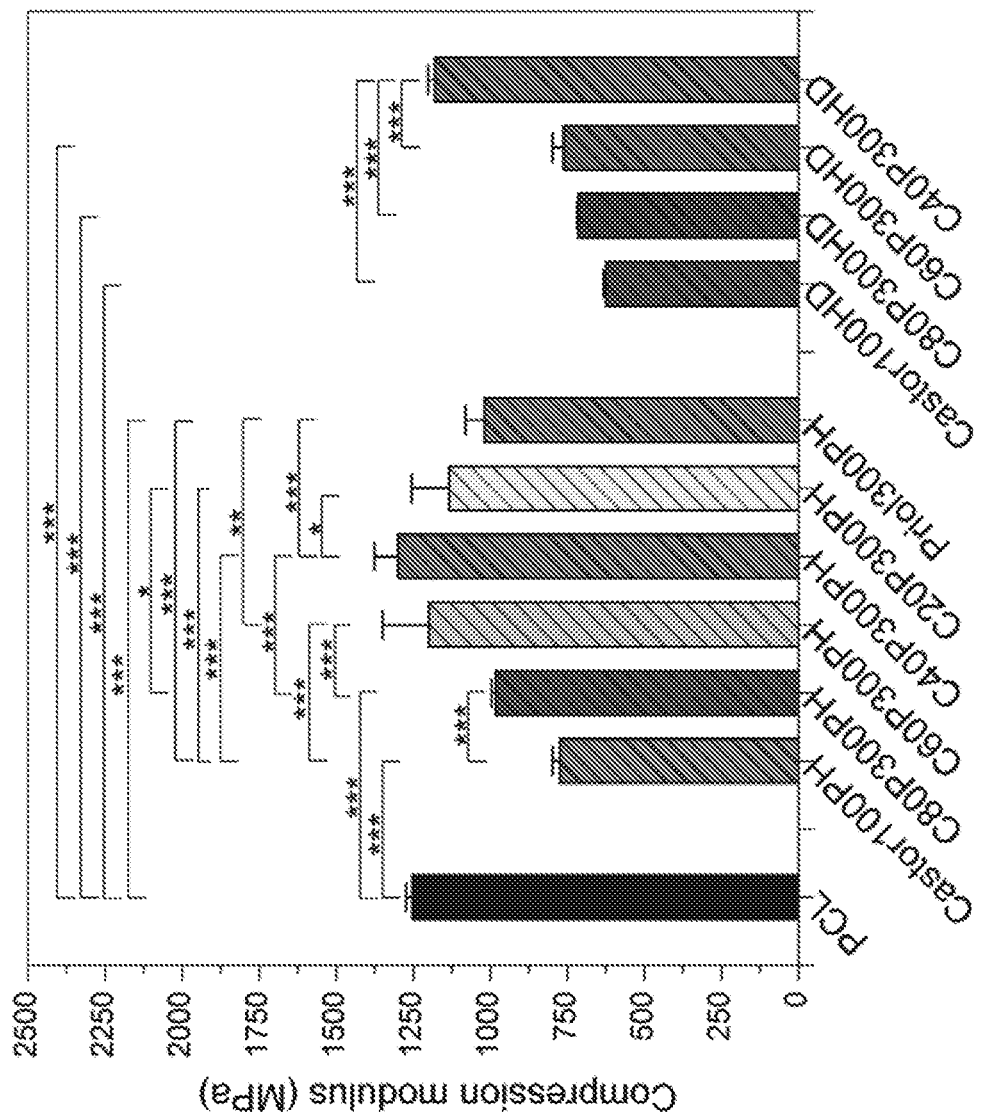
FIG. 6 is a graph showing Compression modulus of synthesized example smart polymers. Data are mean±standard deviation, n=5. * $p<0.05$,  $p<0.01$, and * $p<0.001$

The mechanical behavior of the smart polymers was characterized via uniaxial compression testing and the results are shown in FIG. 6. With PH as the cross-linker, sample C40P300PH showed the highest compression modulus it was also noted that the compressive modulus increased when the weight ratio of castor oil to Ptriol300 decreased to a 40:60 mixture with samples C20P300PH and Ptriol300PH exhibiting a lower modulus than sample C40P300PH. With HD as the cross-linker, sample C40P300PH showed the highest compressive modulus.

Figures 7A, 7B:
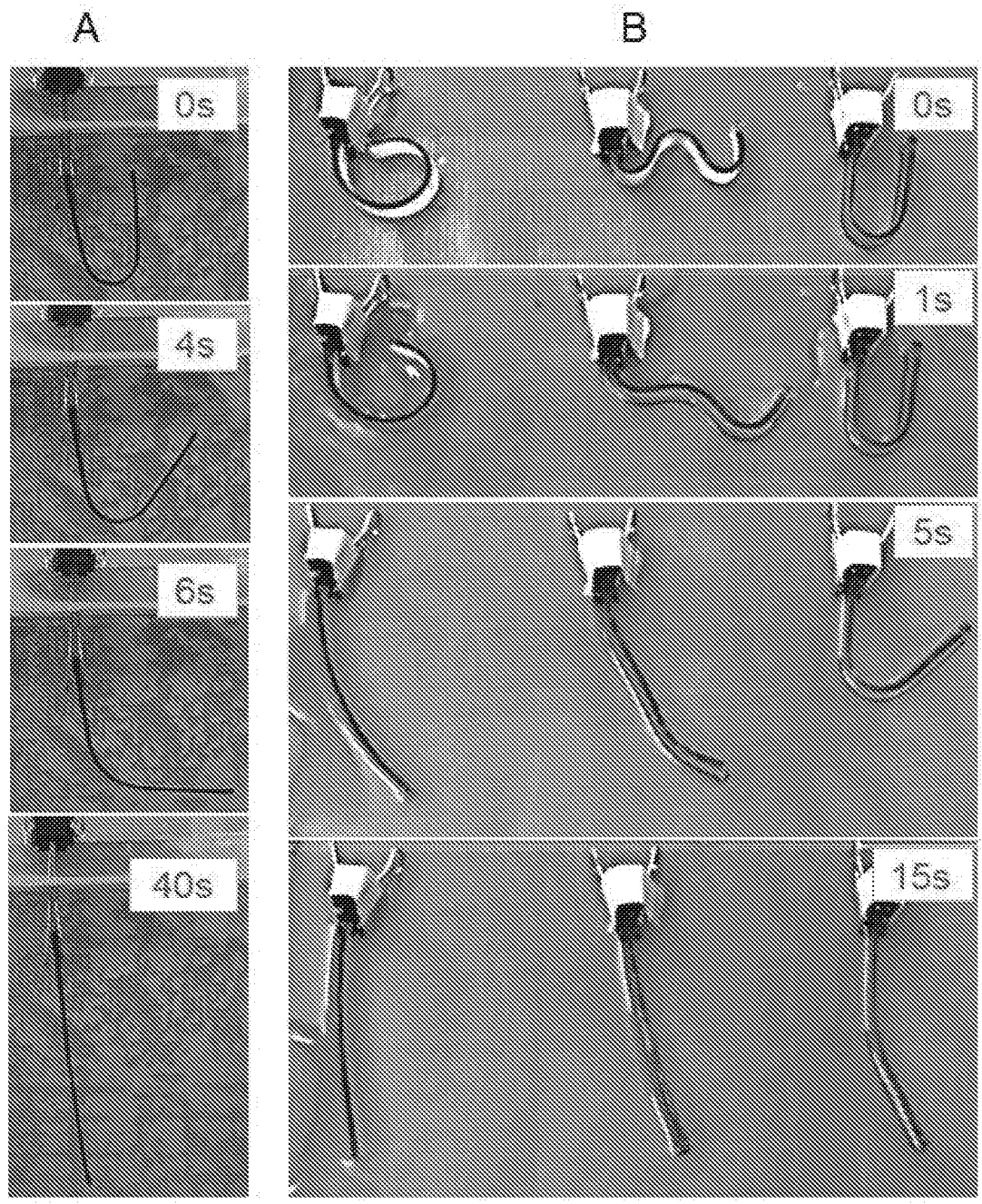
FIG. 7A-7B show images showing the shape memory effects of synthesized example smart polymers: (A) sample C40P300PH was fixed at 0° C. and recovered at 37° C.; (B) samples C80P300PH, C40P300HD and C40P300PH were fixed as "GWU" at −18° C. and recovered at 37° C. with different recovery speed.
Figure 8:
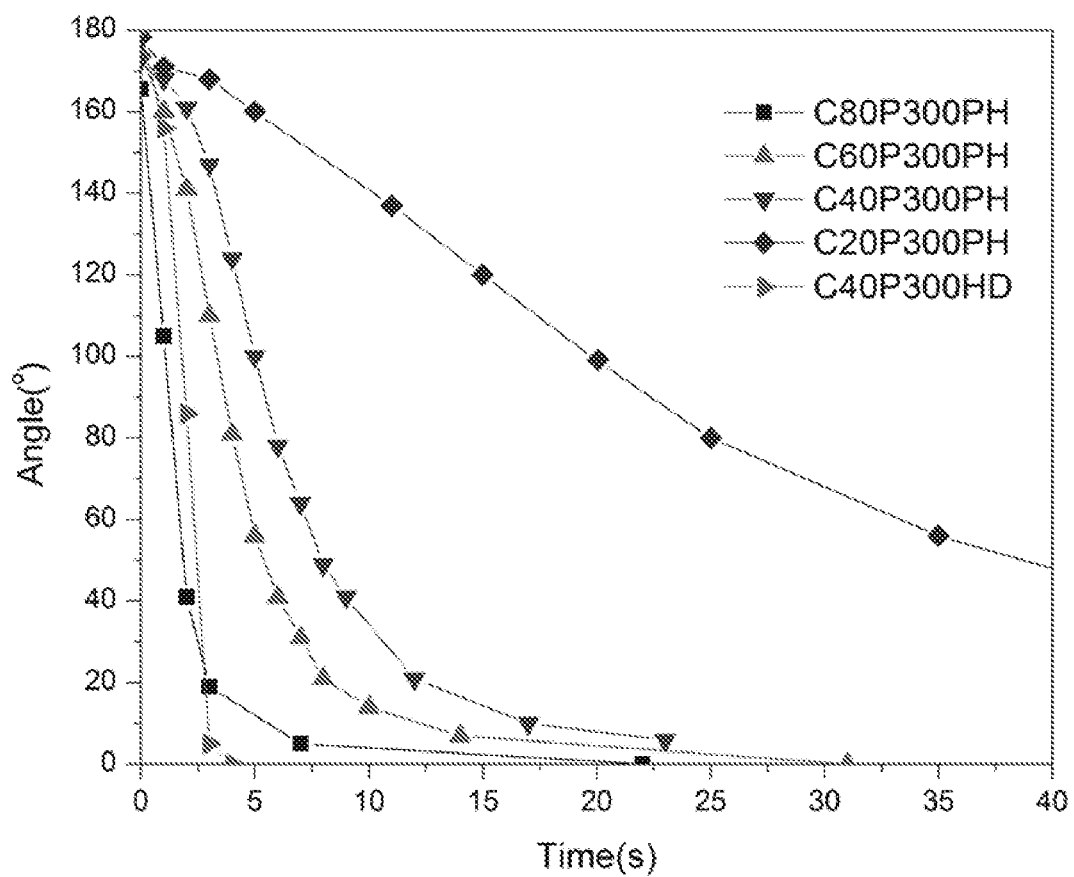
FIG. 8 is a graph showing recovery curves of synthesized example smart polymers which were fixed at −18° C. for a temporary shape and recovered at 37° C. to their permanent shape.

Shape memory effects were evaluated at a recovery temperature of 37° C. based on the intended application of synthesized smart polymers as potential implantable biomaterials. The shape recovery process is illustrated in FIG. 7. As shown in FIG. 7A, sample C40P300PH fully recovers from a programmed "U" shape to its original rectangular shape in 40 s with other smart polymer mixtures displaying recovery speeds ranging from 3.9 to 75.5°/s. As shown in FIG. 7B, samples C80P300PH, C40P300HD and C40P300PH are fixed at −18° C. to "GWU" and restore their permanent shape at various speeds. Sample C40P300PH exhibits an obvious delay in recovery speed when compared to the other two samples. The quantitative recovery speed can be seen in FIG. 8. Full recovery is achieved when the sample recovers its original linear rectangular shape with a bend angle of 0°. Nearly all the samples recover their original shape within 30 s while sample C20P300PH requires approximately three minutes to completely recover. The detailed shape memory effects of the smart polymers are found in Table 2 with all exhibiting excellent shape fixity, shape recovery, and widely adjustable properties with simple alterations in polymer composition.

TABLE 1

Shape memory effects of the synthesized smart polymers

| Sample code | $T_{gc}$ (° C.) | $R_f$ (%) | $R_r$ (%) | Recovery speed (°/s)*[1] |
|---|---|---|---|---|
| C80P300PH | −8 | 92 | 100 | 69.5 |
| C60P300PH | 9 | 97 | 100 | 30.0 |
| C40P300PH | 21 | 96 | 100 | 23.1 |
| C20P300PH | 35 | 99 | 100 | 3.9 |
| C40P300HD | 0 | 100 | 100 | 75.5 |

*[1]Recovery speed, the fastest recovery speed during the recovering

Fabrication of Biomimetic Scaffold

Figures 9A, 9B, 9C, 9D:
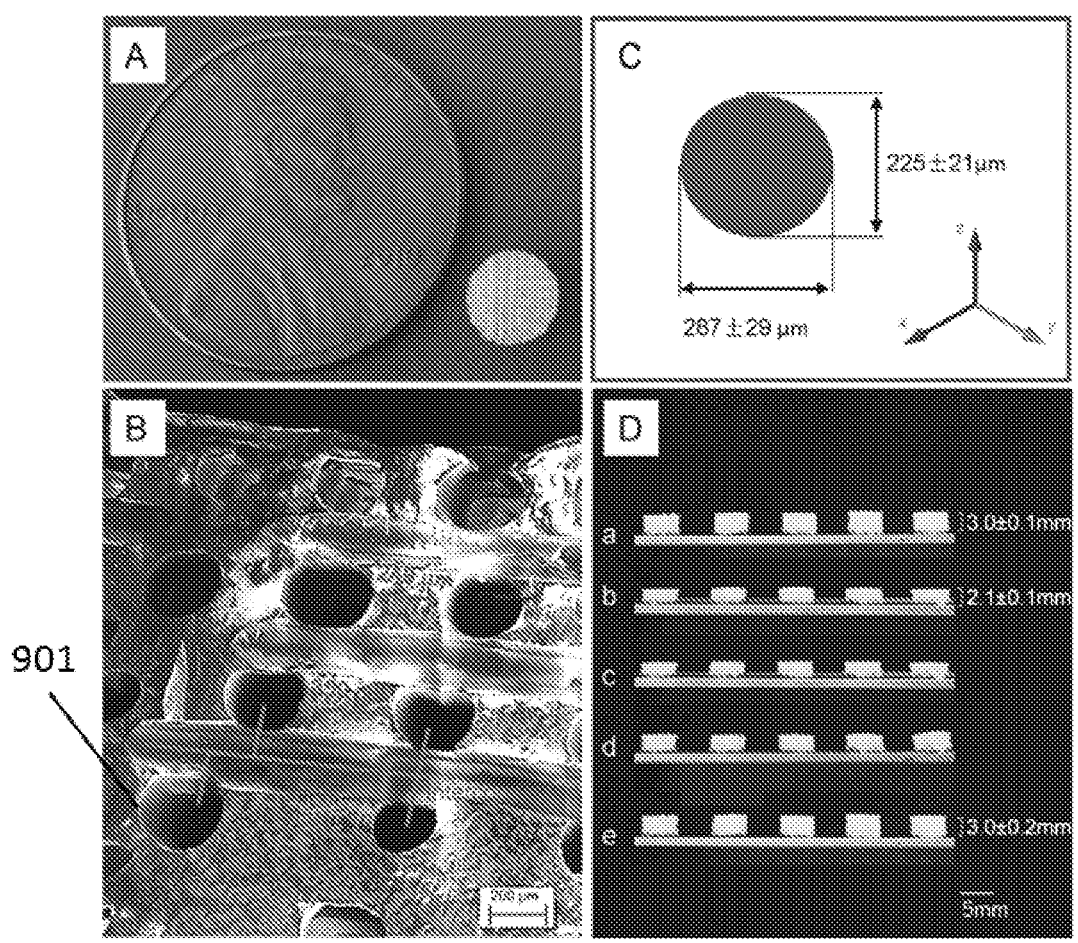
FIG. 9A-9D show images of example scaffolds. (A) A diameter 5 mm and thickness 3 mm scaffold compared to a cent; (B) SEM image of the pore distribution in the scaffold; (C) Varied pore diameter in different direction; (D) The potential for minimally invasive application; a, sample original shape; b, temporary shape at −18° C.; c, 0 s at 37° C.; d, 10 s at 37° C.; e, 3 min at 37° C.; from left to right, the sample is C80P300PH, C60P300PH, C40P300PH, C20P300PH and C40P300HD, respectively.

With a 3D printed PLA scaffold serving as a sacrificial mold, a biomimetic gradient structure was readily obtained with the synthesized smart polymers. Alterations in porosity was achieved by modifying the layer infill density as described in our previous work (25) where FDM printing parameters of the sacrificial mold were correlated to the resultant structure. A greater infill density leads to a tighter printed lattice resulting in a more porous layer after dissolution of PLA. As shown in FIG. 9A, a porous scaffold with a diameter of 5 mm was fabricated. The pores 901 have a gradient distribution from the top to the bottom as the distance between pores increases from 240 to 560 µm, as shown in FIG. 9B. This type of gradient porosity mimics the gradient porosity in natural tissues. In addition, the pores exhibit excellent interconnectivity as seen in FIG. 9B allowing for good nutrient perfusion and waste removal. The diameter of the pores is approximately 250 µm, which can be readily altered by changing the 3D printer nozzle diameter. Pore size distribution is displayed in FIG. 9C. Interestingly, the pore diameter measured in the z-axis is approximately 225 µm while roughly 287 µm in x and y directions. This may be due to deformation of the PLA filament upon extrusion through the high temperature nozzle where PLA is affected by gravity as well as pressure from the flowing material for interlayer adhesion resulting in pore diameter variance. The possibility of employing this system in a minimally invasive surgical procedure was evaluated (FIG. 9D); the fabricated implantable scaffold can be compacted to a thickness of ~70% of original height (from 3.0 mm to 2.1 mm), and can be fully recovered when the scaffold is exposed to physiological temperature.

Bio-Evaluation with MSC

Figure 10:
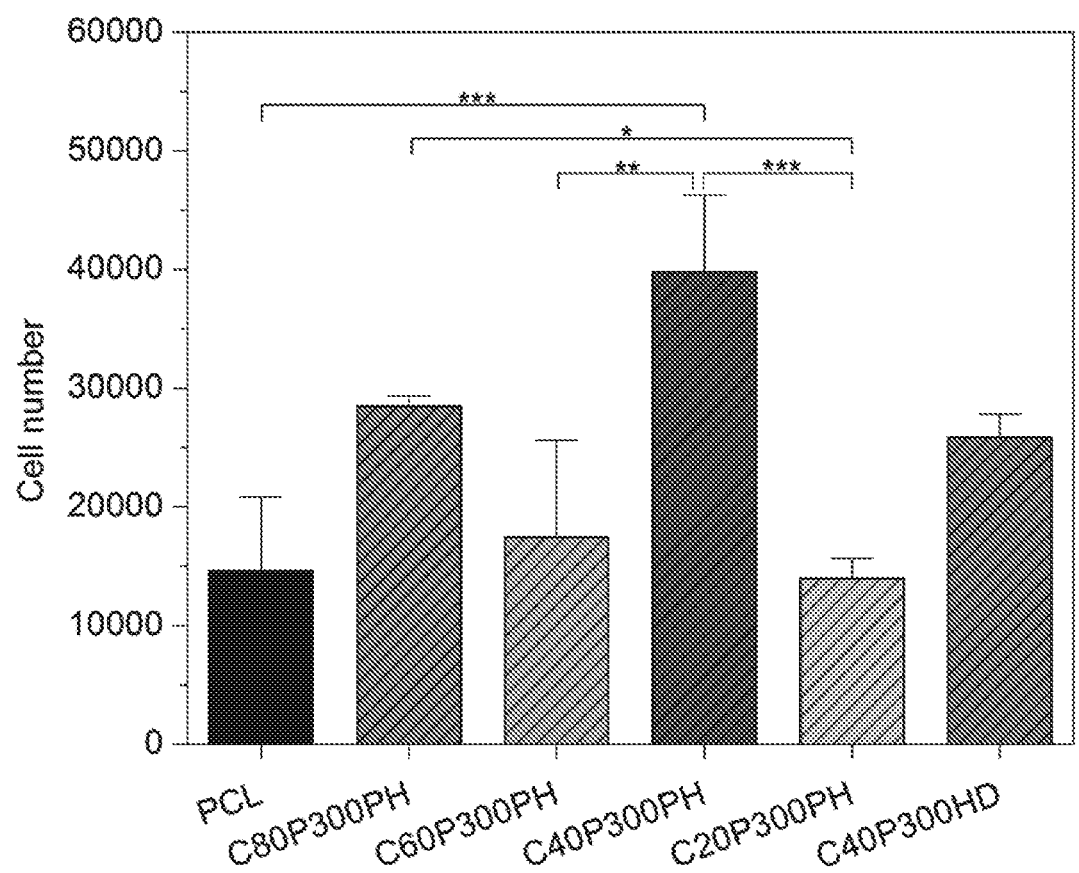
FIG. 10 is a graph showing 4 h adhesion of mesenchymal stem cells (MSCs) on the synthesized example smart polymers. Data are mean±standard deviation, n=6. * p<0.05, p<0.01, and *p<0.001
Figure 11:
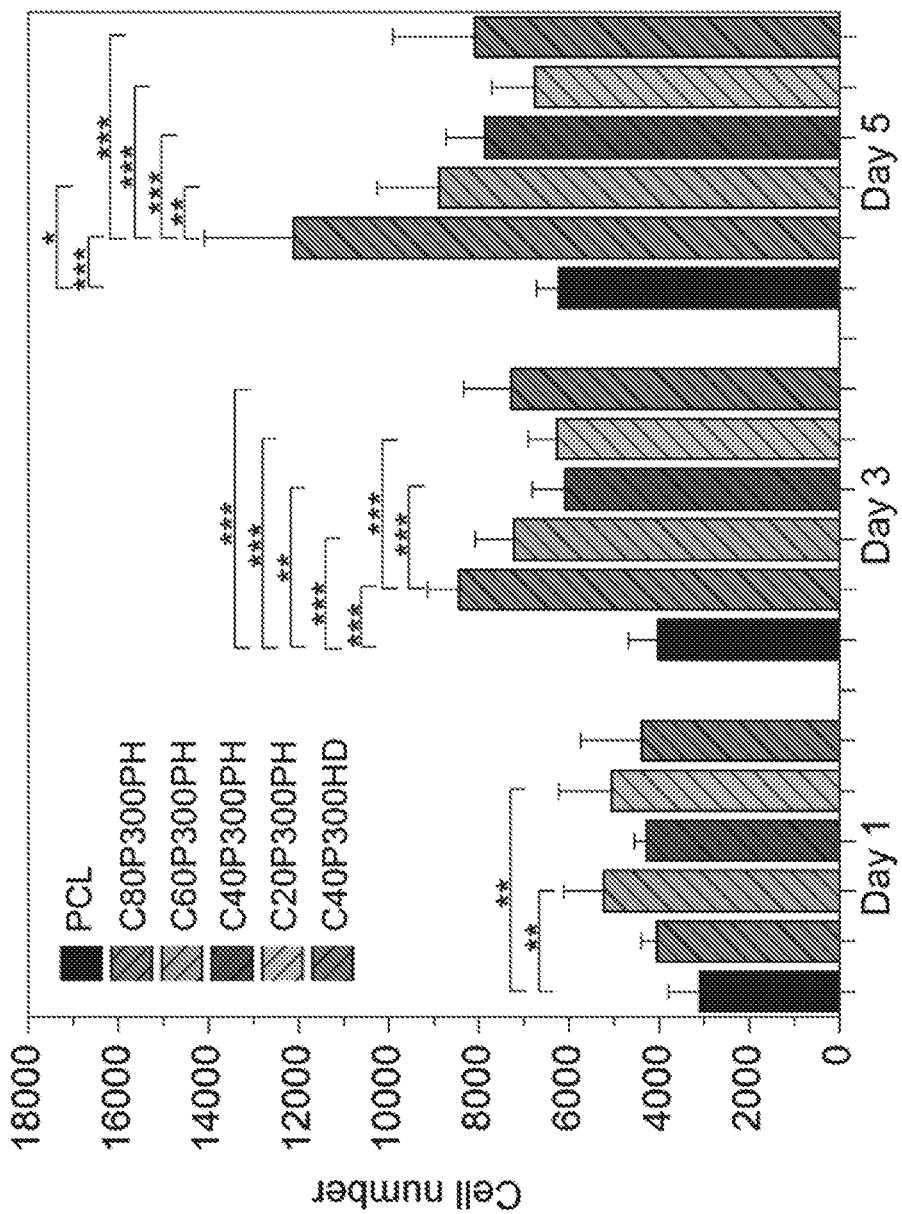
FIG. 11 is a graph showing 1, 3, and 5 day proliferation of MSCs on the synthesized example smart polymers. Data are mean±standard deviation, n=6. *p<0.05, p<0.01, and *p<0.001
Figure 12:
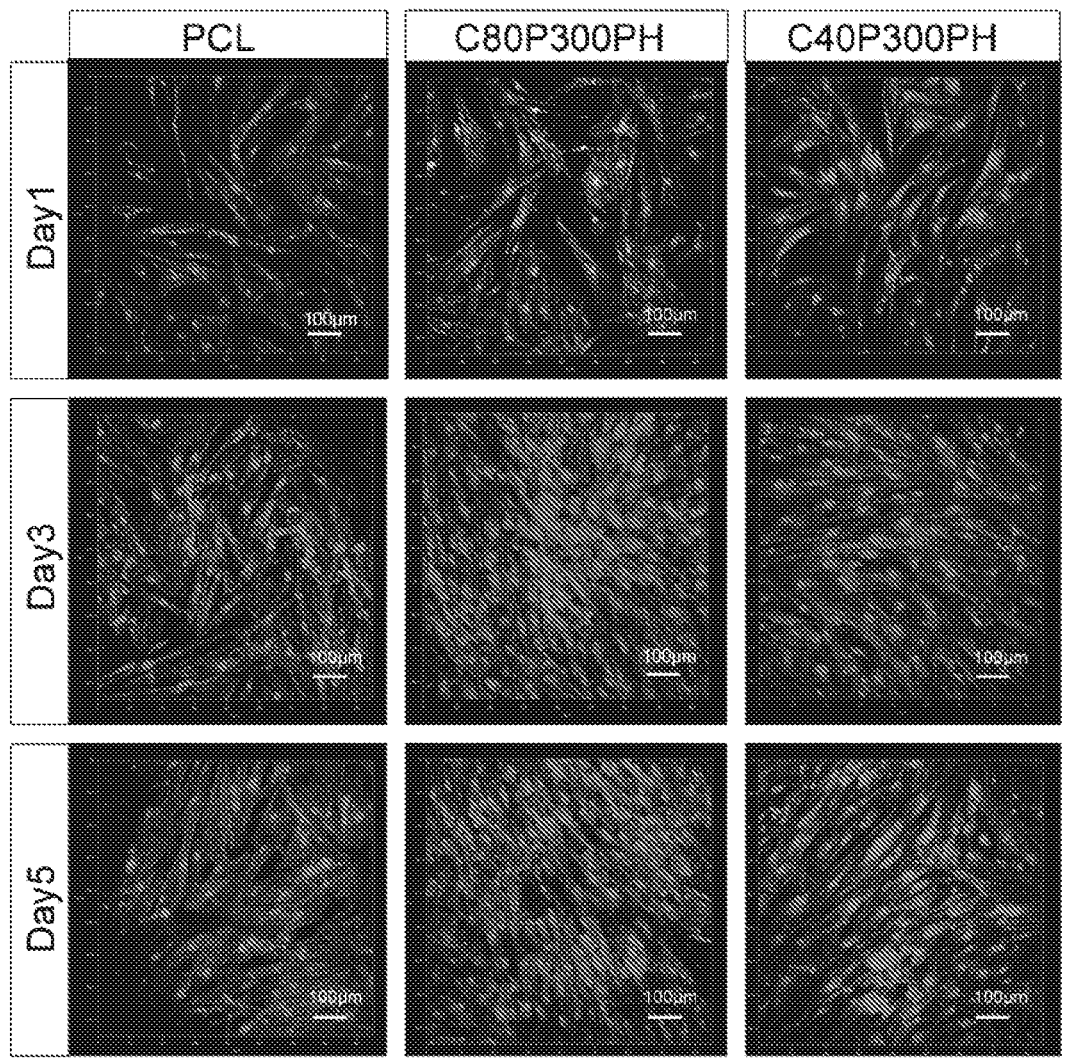
FIG. 12 shows confocal microscopy images of MSC growth and spreading morphology on C40P300PH and C20P300PH when compared with PCL control after 1, 3, and 5 day culture. Cell cytoskeleton and nuclei are shown.
Figure 13:
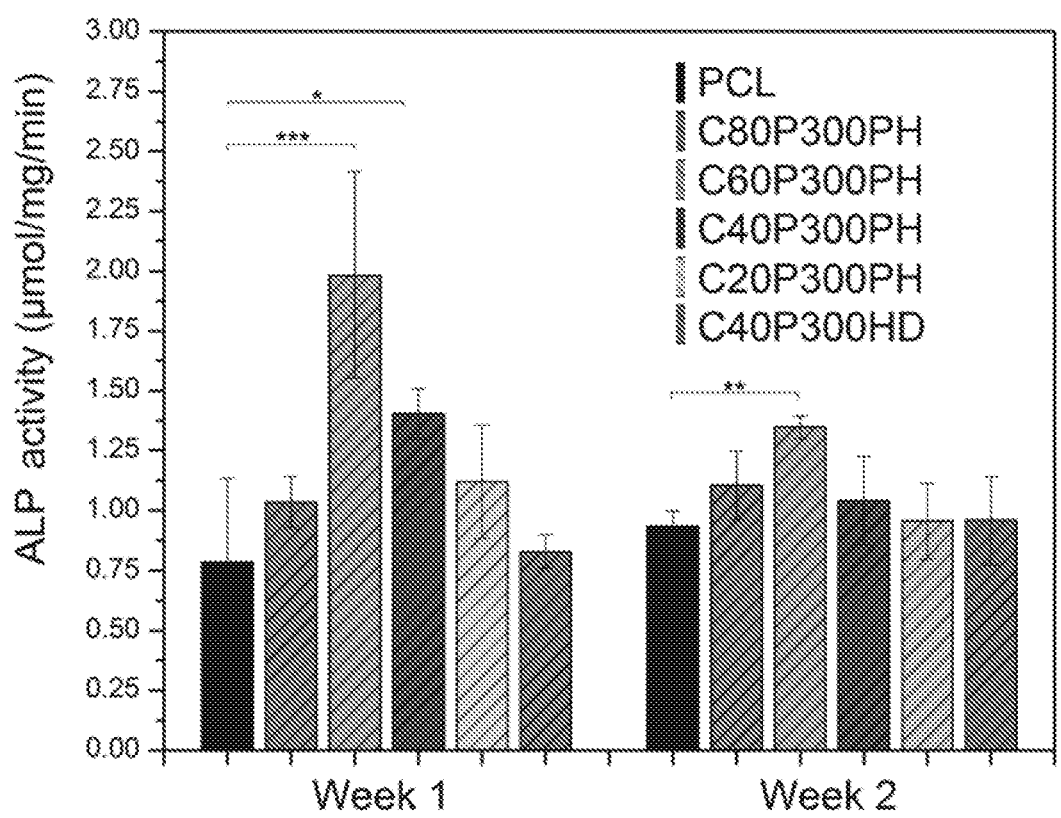
FIG. 13 is a graph showing Alkaline Phosphatase (ALP) activity on different synthesized example smart polymers compared to polycaprolactone (PCL) control. Data are mean±standard deviation, n=6. *p<0.05, p<0.01, and *p<0.001.
Figure 14:
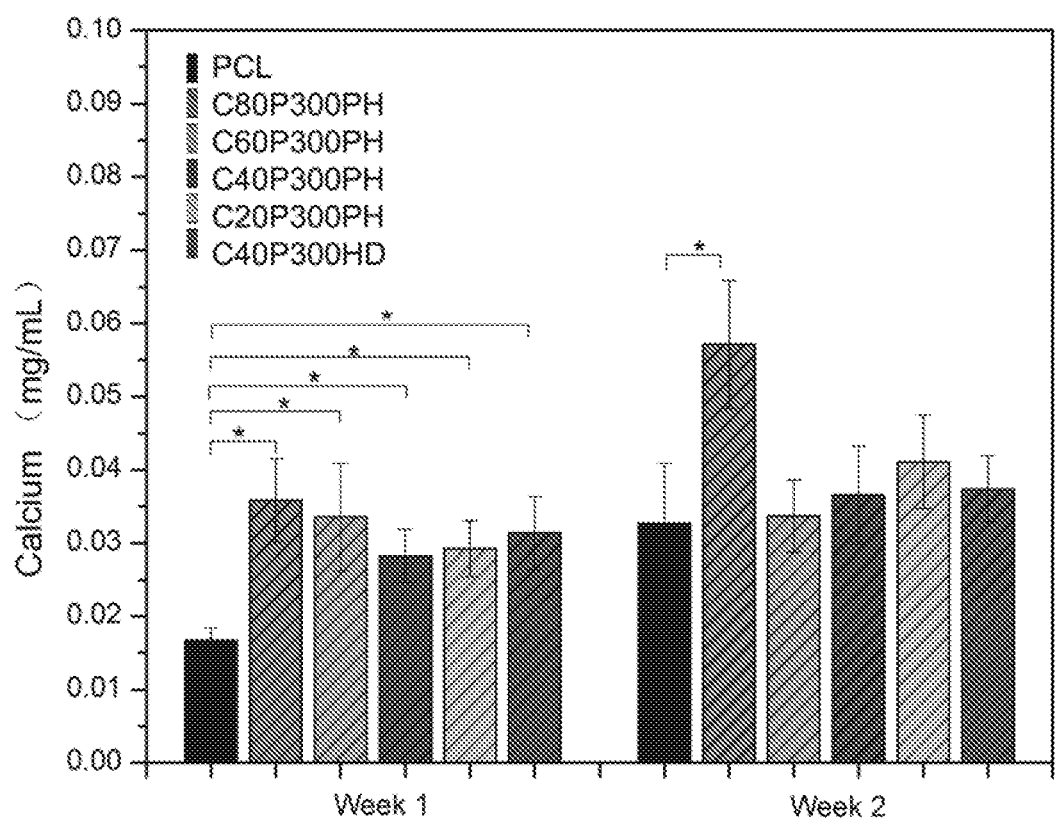
FIG. 14 is a graph showing enhanced total calcium deposition on example smart polymers compared to PCL control. Data are mean±standard deviation, n=6. *p<0.05.

FIG. 10 shows the results of 4 h MSC attachment on PCL control and synthesized smart polymers illustrating that the smart polymers exhibit similar or greater cell attachment when compared to control. Particularly, sample C40P300PH has the highest cell attachment density exhibiting a 1.7, 1.3 and 1.8 fold increase when compared to PCL control, C60P300PH and C20P300PH, respectively. In addition, C80P300PH has significantly better cell attachment than C20P300PH, about a 1 fold increase. FIG. 11 shows MSC proliferation after 1, 3, and 5 day culture on PCL control and the smart polymers. All the samples show excellent MSC proliferation at all time points. Specifically, sample C80P300PH has the highest MSC density with a 110% and 90% increase of cell density when compared to PCL control after 3 and 5 days, respectively. All smart polymers showed significantly higher proliferation when compared to PCL control after 3 days. Another interesting phenomenon is that MSC proliferation increases with increasing castor oil content as seen after 3 and 5 days (FIG. 11). For example, C80P300PH elicited a 35% and 79% increase in MSC density when compared to C20P300PH after 3 and 5 days, respectively. Increased cell proliferation was qualitatively evaluated by confocal analysis as shown in FIG. 12. Both C80P300PH and C40P300PH exhibited excellent cell spreading morphology and increased cell growth density when compared to PCL control. FIG. 13 shows the ALP activity of MSC differentiation on various sample groups. The samples C60P300PH and C40P300PH showed significantly higher ALP activity than PCL control on week 1; only sample C60P300PH showed greater ALP specific activity when compared to PCL control on week 2. FIG. 14 shows the calcium deposition on different materials. All the smart materials exhibited significant higher calcium deposition than PCL control on week 1; only sample C40P300PH had greater calcium deposition than PCL control on week 2.

Discussion

The shape memory functionality of synthesized smart polymers is highly dependent upon the material composition. Although both Ptriol300 and Ptriol900 were utilized to synthesize the polymeric networks, only Ptriol300 based samples display a shape memory effect. Both HD and PH are capable of fully cross-linking the polymers where gel contents of the polymeric networks are greater than 95%. Amongst the 22 synthesized polymers, five are capable of temporary shape fixation at 0 or −18° C. with four of the five using PH as the cross-linking agent. In the polymeric networks, the cross-linking net points are intended to maintain the original shape while the glass transitions provide the mechanism for temporary shape fixation. The networks based on Ptriol300 and PH provide a suitable glass transition to perform the shape fixity effect under the intended test conditions.

Uniaxial compression tests indicate the presence of interpenetrating polymeric networks (IPNs). Two networks are present in the synthesized smart polymers: network I (castor oil+PH), network II (Ptriol300+PH). When the weight ratio of castor oil to Ptriol300 is greater than 40:60, network I is dominant; when the ratio is lower than 40:60, network II is the main cross-linking structure; in sample C40P300PH, networks I and II are both fully cross-linked, resulting in a complete IPN. It is a typical phenomenon that IPNs can exhibit enhanced properties than both substituent polymers alone due to inter net-locking structures (26, 27). Similar results are observed when HD is used as the cross-linker. The compression modulus of sample C40P300HD is significantly higher than others although Ptriol300HD is not formed due to reagent immiscibility. The IPNs structure can also be used to interpret DSC results. Network I tends to exhibit a lower $T_g$ while network II tends to shift the $T_g$ to a higher temperature range. For example, sample C40P300PH exhibits full cross-linking of both networks I and II which has a tendency to keep both glass transitions and results in a broader $T_g$ breadth.

Sample C40P300PH exhibits significantly higher MSC attachment when compared to PCL control. The attachment of MSCs is affected by multiple parameters, including surface hydrophobicity, surface morphology, material toughness, and chemical composition. Water contact angle analysis suggests that the hydrophobicity of the smart polymers is not statistically different than PCL. SEM analysis shows that there is no significant difference between sample C40P300PH's surface and other samples' surfaces. Sample C40P300PH shows higher compression modulus than other smart polymer samples, but is close to that of PCL. Taken collectively, it can be postulated that the increased cellular attachment is chemically mediated by the composition of the newly synthesized smart polymers. In addition to the presence of Ptriol300 segments which are structurally similar to PCL, the smart polymers contain urea and urethane groups (FIG. 2) which may contribute to improved MSC attachment.(28)

The smart polymers with higher castor oil content show significantly higher MSC proliferation when compared to PCL control and smart polymers with lower castor oil content at 3 and 5 days. The greater MSC proliferation may be attributed to the combined effects of mechanical and chemical properties of the samples as described above. An interesting observation was made when samples containing a higher content of castor oil (higher content of polymeric network I) leading to greater MSC proliferation. Sample C80P300PH shows the highest proliferation rate with this sample having more castor oil than other smart polymers and PCL control. Therefore, MSCs may prefer a predominant castor oil network. These findings lend themselves to further studies of copolymers from PCL and plant oils for smart tissue applications.

ALP is a known in vitro osteogenic differentiation marker. (29) The increase of ALP activity on the synthesized smart polymers indicates their great potential as bone regenerative materials. Sample C60P300PH showed significantly higher ALP activity than PCL control on both weeks 1 and 2. The enhanced MSC differentiation on the week 1 is further confirmed by calcium deposition. Similar to MSC proliferation, the enhanced MSC differentiation may be attributed to the combined effects of mechanical and chemical properties as well as the effect of plant oil residue within the polymer leading to greater interest of plant oil-based materials for biomedical applications.

The 4D printing technique employed here will further advance the application of 3D technology in fabricating shape memory scaffolds with thermosetting polymers. 3D printing technologies are vastly increasing in popularity due to the ability to directly print porous scaffolds with designed shape and interconnected porosity from a CAD file from a variety of materials such as ceramic, metallic, polymeric, and composite materials. Biopolymers are particularly important due to their excellent biocompatibility and functionality. Among 3D printing techniques, fused deposition modeling (FDM) is one of the most applied and commercialized technologies.(30, 31) Typically, a thermoplastic filament material is forced out of a temperature-controlled extruder, and the molten polymer is deposited on a platform layer by layer. However, thermosetting polymers cannot be melted and reshaped after they are cured, which is very different from traditional 3D printable thermoplastic polymers.(32) Therefore, thermosetting polymers are largely incompatible with FDM based printers.(33) Instead, fully controlled gradient scaffolds can be fabricated by curing thermosetting polymers with FDM printed sacrificial molds as demonstrated in this study. Another advantage of this guided approach is in providing different pore morphology. Generally, direct 3D printing techniques contain inherent difficulties to form small sized tubular channels around 250 μm(34), the pores in the FDM printed scaffold from the guided approach here are actually the shape of the extruded fiber which can be readily adjusted by shaping the size and geometry of the nozzle(35). The channel-like pore structure may provide better conditions for vascularization in view of the similarity between tubular channels and blood vessels, which extends beyond the scope of this study.

CONCLUSION

The synthesized smart polymers, which have close compression modulus and surface hydrophobicity to PCL, exhibit excellent shape memory effects with various recovery speeds at physiological temperature from a fixed temporary shape. When combined with a sacrificial 3D printed PLA mold, scaffolds of graded porosity and shape memory effect can be readily fabricated, which provides a facile method for developing complex graded scaffolds for tissue engineering applications. This 4D printing technique not only provides gradient distributed channel morphology, but also illustrates the great potential of 4D technology in developing scaffolds from thermosetting polymers which are not printable with FDM-based 3D printers. All the smart polymers exhibit excellent attachment, proliferation and differentiation of MSCs. The excellent shape memory effect, extraordinary cytocompatibility and complex graded structure illustrate the great potential for regenerative medicine applications.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A shape memory polymer composition comprising
   a cross-linker molecule comprising at least two isocyanate groups;

a natural oil comprising a hydroxyl group cross-linked to at least one of the at least two isocyanate groups, thereby forming a natural oil-based polymeric network; and a biocompatible polymer selected from the group consisting of polycaprolactone diol, polycaprolactone triol, polylactide diol, or polylactide triol, the biocompatible polymer comprising a hydroxyl group cross-linked to at least one of the at least two isocyanate groups, thereby forming a biocompatible polymer-based polymeric network, wherein a molar ratio of the hydroxyl group to the isocyanate group is 1:1.05;

wherein the natural oil and the biocompatible polymer are cross-linked to different isocyanate groups; and wherein the natural oil and the biocompatible polymer are cross-linked to the cross-linker molecule such that a thermoset polymer is formed.

2. The shape memory polymer composition of claim 1, wherein each of said at least two isocyanate groups of said cross-linker molecule is cross-linked with either said hydroxyl group of said natural oil or said hydroxyl group of said biocompatible polymer.

3. The shape memory polymer composition of claim 1, wherein said cross-linker molecule is selected from the group consisting of hexamethylene diisocyanate, poly(hexamethylene diisocyanate), isophorone diisocyanate, 1,4-phenylene diisocyanate, 1,3-phenylene diisocyanate, m-xylene diisocyanate, tolylene-2,4-diisocyanate, or tolylene-2,6-diisocyanate.

4. The shape memory polymer composition of claim 1, wherein said biocompatible polymer is selected from the group consisting of polycaprolactone, polylactide, or polyethylene glycol.

5. The shape memory polymer composition of claim 1, wherein said natural oil is selected from the group consisting of a castor oil, a soybean oil based polyol, a linseed oil based polyol, a corn oil based polyol, a cottonseed oil based polyol, a palm oil based polyol, a peanut oil based polyol, a rapeseed oil based polyol, or a sunflower oil based polyol.

6. The shape memory polymer composition of claim 1, further comprising a weight ratio of said natural oil to said biocompatible polymer of between 80:20 and 20:80.

7. The shape memory polymer composition of claim 1, wherein said biocompatible polymer has an average molecular weight (Mn) of at most 900.

8. The shape memory polymer composition of claim 1, wherein said biocompatible polymer has an average molecular weight (Mn) of between 300 and 900.

* * * * *